US008501683B2

(12) United States Patent
Wenger et al.

(10) Patent No.: US 8,501,683 B2
(45) Date of Patent: Aug. 6, 2013

(54) CYCLOUNDECADEPSIPEPTIDE COMPOUNDS AND USE OF SAID COMPOUNDS AS A MEDICAMENT

(75) Inventors: Roland Wenger, Riehen (CH); Manfred Mutter, Belmont-Sur-Lausanne (CH); Patrick Garrouste, Saxon (CH); Robert Lysek, Martigny (CH); Olivier Turpin, Martigny (CH); Grégoire Vuagniaux, Lausanne (CH); Valérie Nicolas, St-Prex (CH); Laura Novaroli Zanolari, Lausanne (CH); Rafael Crabbé, Bursins (CH)

(73) Assignee: Debio Recherche Pharmaceutique S.A., Martigny (CH)

( * ) Notice: Subject to any disclaimer, the term of this patent is extended or adjusted under 35 U.S.C. 154(b) by 159 days.

(21) Appl. No.: 12/998,588

(22) PCT Filed: Nov. 6, 2009

(86) PCT No.: PCT/IB2009/007361
§ 371 (c)(1),
(2), (4) Date: May 5, 2011

(87) PCT Pub. No.: WO2010/052559
PCT Pub. Date: May 14, 2010

(65) Prior Publication Data
US 2011/0212057 A1    Sep. 1, 2011

(30) Foreign Application Priority Data

Nov. 6, 2008  (WO) .................. PCT/IB2008/002982

(51) Int. Cl.
*A61K 38/12*       (2006.01)
(52) U.S. Cl.
USPC ......................................... 514/4.3; 514/21.1

(58) Field of Classification Search
None
See application file for complete search history.

(56) References Cited

U.S. PATENT DOCUMENTS

| 5,116,816 A | * | 5/1992 | Dreyfuss et al. ............. 514/20.5 |
| 2004/0161399 A1 | | 8/2004 | Kim et al. |
| 2006/0252675 A1 | | 11/2006 | Scalfaro et al. |
| 2007/0275884 A1 | | 11/2007 | Hijikata et al. |
| 2009/0081164 A1 | | 3/2009 | Scalfaro et al. |

FOREIGN PATENT DOCUMENTS

| WO | WO-02092033 A1 | 11/2002 |
| WO | WO-2005021028 A1 | 3/2005 |
| WO | WO-2006038088 A1 | 4/2006 |

OTHER PUBLICATIONS

Hansson M J et al: "The nonimmunosuppressive cyclosporin analogs NIM811 and UNIL025 display nanomolar potencies on permeability transition in brain-derived mitochondria" Journal of Bioenergetics and Biomembranes, Plenum Publishing, New York, NY, US, vol. 36, No. 4, Aug. 1, 2004, pp. 407-413, XP002330699, ISSN: 0145-479X the whole document.

Nakagawa M et al: "Specific inhibition of hepatitis C virus replication by cyclosporin A" Biochemical and Biophysical Research Communications, Academic Press Inc. Orlando, FL, US, vol. 313, No. 1, Jan. 2, 2004, pp. 42-47, XP004479114 ISSN: 0006-291X the whole document.

International Search Report for PCT/IB2009/007361 dated Mar. 4, 2010.

* cited by examiner

*Primary Examiner* — Christina Bradley
(74) *Attorney, Agent, or Firm* — Harness, Dickey & Pierce, P.L.C.

(57) ABSTRACT

At least one embodiment of the present invention relates to new cycloundecadepsipeptide compounds and to the use of said compounds as a medicament, in particular as antiviral agents, more particularly for preventing or treating Hepatitis C infections or HCV induced disorders.

18 Claims, 1 Drawing Sheet

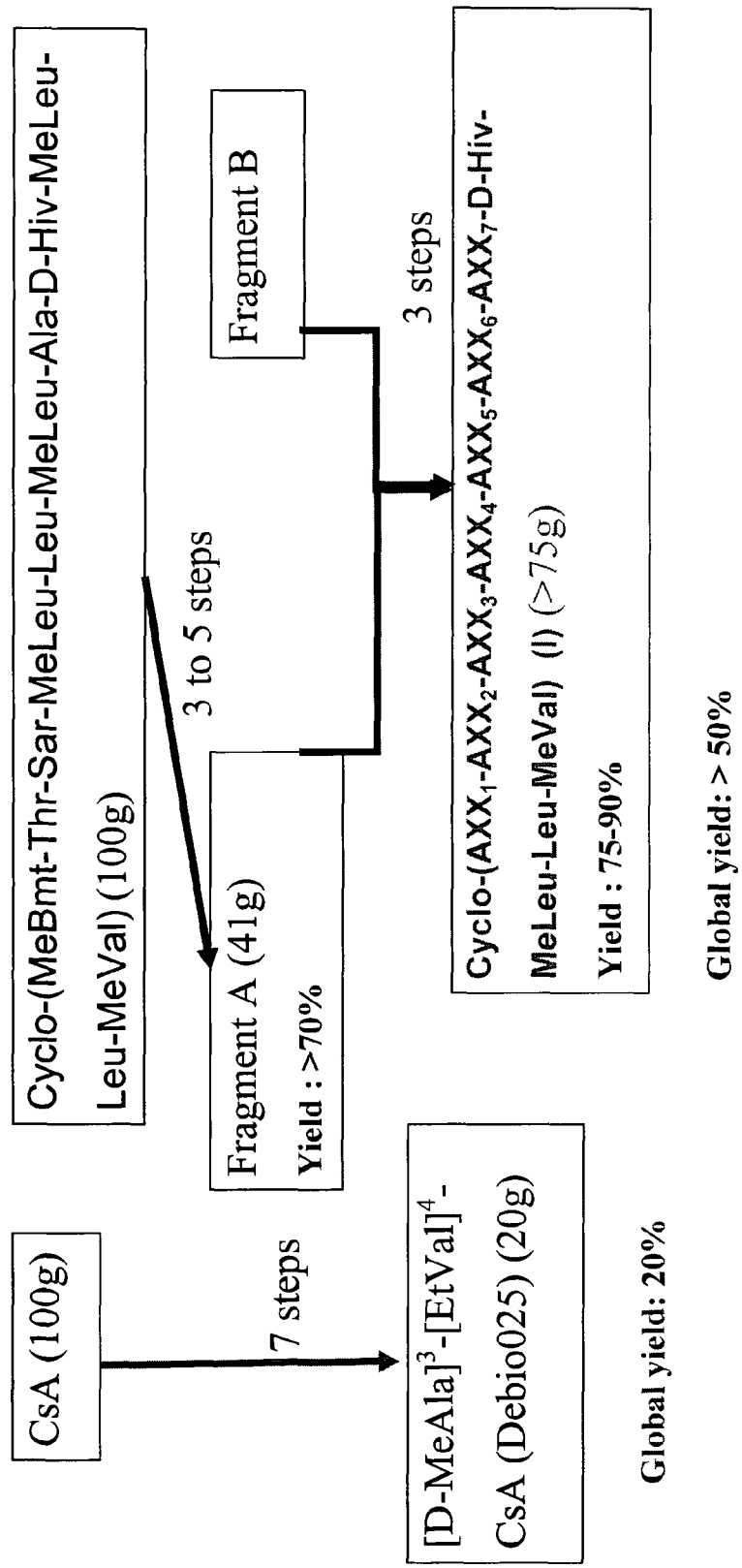

CYCLOUNDECADEPSIPEPTIDE COMPOUNDS AND USE OF SAID COMPOUNDS AS A MEDICAMENT

The present invention relates to cycloundecadepsipeptide compounds. It also relates to the use of these compounds as a medicament, in particular as antiviral agents, more particularly for preventing or treating Hepatitis C infections or HCV induced disorders.

BACKGROUND ART

HCV was cloned and characterized about 15 years ago by Choo and colleagues (see Science 244, (1989), 359-362). HCV belongs to the family Flaviviridae and comprises an enveloped nucleocapsid and a single-stranded RNA genome of positive polarity (see Bartenschlager et al., Antiviral Res. 60, (2003), 91-102). HCV is transmitted primarily by blood, blood products and vertical transmission during pregnancy. Introduction of diagnostic tests for screening blood products has significantly reduced the rate of new infection.

Still, HCV remains a serious medical problem. There are currently about 170 million people infected with HCV. The initial course of infection is typically mild. However, the immune system is often incapable of clearing the virus, and people with persistent infections are at a high risk for liver cirrhosis and hepatocellular carcinoma (see Poynard et al., Lancet 349, (1997), 825-832).

There is no vaccine available, and therapeutic options are very limited (see Manns et al., Indian J. Gastroenterol. 20 (Suppl. 1), (2001), C47-51; Tan et al., Nat. Rev. Drug Discov. 1, (2002), 867-881).

Compounds which bind strongly to cyclophilin have been identified but those compounds were immunosuppressive (Nakagawa M et al., Biochemical and biophysical research communications, Academic Press Inc. Orlando, Fla., US, Vol. 313, N° 1, 2 Jan. 2004, pages 42-47, XP004479114).

Therefore, during the last 20 years, a number of medicinal chemistry studies have been conducted with the aim to identify non-immunosuppressive compounds such as NIM 811 or other compounds presenting also a high potency to inhibit HIV-1 replication and essentially lacking of immunosuppressive activity, see WO 00/01715 (Wenger et al.; DEBIOPHARM SA) and Tetrahedron Lett., 41, (2000), 7193-6.

It has been found that non-immunosuppressive compounds which bind to cyclophilin have an inhibitory effect on Hepatitis C virus (HCV). Persistent infection by HCV, which has been identified as the major causative agent of non-A, non-B hepatitis has been considered closely related to liver diseases such as chronic hepatitis, liver cirrhosis or hepatocellular carcinoma. The development of these liver diseases is a major public health problem. Effective anti-HCV therapy is restricted to therapy with interferon or a combination of interferon and ribavirin. However, since the virus is not eliminated from about a half of the HCV patients treated with these known agents, there is still a strong need for alternative anti-HCV agents.

Cycloundecapeptides having the property to act on inhibition of hepatitis C virus (HCV) replication are already known from WO 2005/021028 (Novartis Pharma GMBH) and WO 2006/038088 (DEBIOPHARM SA). Hanssons M J et al. Journal of Bioenergetics and biomembranes, plenum publishing, New York, N.Y., US, Vol. 36, n° 4, 1 Aug. 2004, pages 407-413 (XP002330699) reports the better potencies of mPT inhibition by the compounds described in WO 2006/038088. However although some of these peptides are presently involved in clinical trials, there is still a need to develop new antiviral agents having satisfactory property to inhibit the replication of, in particular, HCV, along with improved pharmacokinetic profile (e.g. hepatic transporter inhibition profile and resulting drug-drug interactions) and with improved toxicology profile (e.g. non-immunosuppressive activity, and resulting adverse events).

Accordingly, the present invention aims to provide further non-immunosuppressive compounds to be used in the prevention or treatment of Hepatitis C infections or HCV induced disorders. Those compounds have the unexpected advantage either to reduce the potential adverse effects related to the inhibition of hepatic transporters or the potential drug-drug interactions related to the inhibition of hepatic transporters or even both. In addition it is also an object of the invention to provide compounds that are easier to synthesize in particular at an industrial scale.

BRIEF DESCRIPTION OF THE INVENTION

Therefore the aim of the present invention was to provide new antiviral agents having the above-mentioned improved properties and surprisingly it has been found that these requirements are fulfilled by cycloundecadepsipeptide compounds, as defined in Formula (I)

(I)

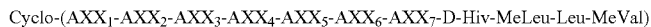

Cyclo-($AXX_1$-$AXX_2$-$AXX_3$-$AXX_4$-$AXX_5$-$AXX_6$-$AXX_7$-D-Hiv-MeLeu-Leu-MeVal)

1      2      3      4      5      6      7      8      9   10   11 in which $AXX_1$ is MeBmt, 4-fluoro-MeBmt, dihydro-MeBmt, 8-hydroxy-MeBmt; O-acetyl-MeBmt;

$AXX_2$ is Abu, Val, Thr, Thr(OMe), Thr(OAc), Thr(OCOCH$_2$CH$_2$CH$_2$OH), Nva, 5-hydroxy-Nva;

$AXX_3$ is D-MeAla, D-3-fluoro-MeAla, D-MeSer, D-MeSer(OAc), D-MeSer(O—CH$_2$CH$_2$OH), D-MeSer(OCH$_2$CH$_2$NEt$_2$), D-MeAsp(OMe);

$AXX_4$ is MeIle, MeMet, MeMet(Ox) with Ox meaning that sulphur atom of methionine is sulphoxyde or sulphone, MeVal, MeThr, MeThr(OAc), MeThr(OtBu), MeThr(OMe), MeAla, MeIle, MeThr, EtVal, EtIle, EtPhe, EtTyr, EtThr(OAc), MeThr(OAc), MeTyr, MeTyr(OAc), MeTyr(OMe), MePhe;

$AXX_5$ is Leu, Val, Ile, Ala;

$AXX_6$ is MeAla, Sar, MeLeu; and $AXX_7$ is Gly, Ala.

Another object of the invention is to provide for a pharmaceutical composition for preventing or treating Hepatitis C infections or HCV induced disorders, comprising the compound of formula I, together with one or more pharmaceutically acceptable diluents or carriers.

A further object of the invention is to provide a pharmaceutical combination comprising at least a) a first agent consisting of the compounds of formula I or the pharmaceutical composition, and b) a second agent having properties to act against HCV replication.

Compounds according to Formula I may be used in the manufacture of a medicament in the treatment of prevention of Hepatitis C infections or HCV induced disorders.

A yet further object of the invention is to provide a method for preventing or treating Hepatitis C infections or HCV induced disorders in a subject in need thereof, comprising administering to said subject a therapeutically effective amount of the compounds of Formula I or the pharmaceutical composition according to the invention.

Alternatively a method for inhibiting HCV replication in a patient in need thereof, comprising administering to said subject a therapeutically effective amount of the compounds of Formula I or the pharmaceutical composition of the invention are also provided.

BRIEF DESCRIPTION OF THE FIGURES

For a better understanding of the invention and to show how the same may be carried into effect, there will now be shown by way of example only, specific embodiments, methods and processes according to the present invention with reference to the accompanying drawings in which:

FIG. 1 shows the chemical synthesis of the compounds according to the invention in comparison to compound according to WO 2006/038088 i.e. [D-MeAla]$^3$-[EtVal]$^4$-CsA (Debio 025).

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

As used herein, the following definitions are supplied in order to facilitate the understanding of the present invention.

The term "comprise" is generally used in the sense of include, that is to say permitting the presence of one or more features or components.

It is an object of the present invention to provide for a cycloundecadepsipeptide compound of Formula (I)

in which:

AXX$_1$ is MeBmt, 4-fluoro-MeBmt, dihydro-MeBmt, 8-hydroxy-MeBmt; O-acetyl-MeBmt;

AXX$_2$ is Abu, Val, Thr, Thr(OMe), Thr(OAc), Thr(OCOCH$_2$CH$_2$CH$_2$OH), Nva, 5-hydroxy-Nva;

AXX$_3$ is D-MeAla, D-3-fluoro-MeAla, D-MeSer, D-MeSer(OAc), D-MeSer(O—CH$_2$CH$_2$OH), D-MeSer(O—CH$_2$CH$_2$NEt$_2$), D-MeAsp(OMe);

AXX$_4$ is MeIle, MeMet, MeVal, MeThr, MeThr(OAc), MeAla, EtVal, EtIle, EtPhe, EtTyr, EtThr(OAc), MeThr(OAc), MeTyr, MeTyr(OAc), MeTyr(OMe), MePhe, MeMet(Ox) wherein the sulphur atom of methionine is sulphoxyde or sulphone;

AXX$_5$ is Leu, Val, Ile;

AXX$_6$ is MeAla, Sar, MeLeu; and

AXX$_7$ is Gly, Ala.

According to IUPAC admitted definition, cyclodepsipeptides are natural or synthetic compounds having sequences of amino and hydroxyl carboxylic acid residues (usually α-amino and α-hydroxy acids) and the residues are connected in a ring (see IUPAC Compendium of Chemical Terminology, 2$^{nd}$ Edition (1997). Such cyclodepsipeptides are depicted as heterodetic peptides in which at least one amide bond has been replaced with an ester bond (see J. Peptide Sci. 10: 115-8 (2004)).

The compounds of the present invention comprise eleven residues, ten being α-amino acids and one being α-hydroxy acid. This α-hydroxy acid is (2R)-2-hydroxy-3-methyl-butanoic acid, also known as D-α-hydroxyisovaleric acid and abbreviated as H-D-Hiv-OH. In Formula (I), this hydroxyl acid is in position 8. It forms on the carboxylic acid end an amide bond with the amino group of the α-amino acid in position 9, namely N-methyl-leucine, and, on the hydroxyl end an ester bond with the carboxylic acid group of the α-amino acid in position 7, namely alanine or glycine.

The α-amino acids of Formula (I) are mentioned using the three letter code abbreviation usually used to name amino acids and their configuration is L-configuration, unless otherwise specified. The residue numbering starts from AXX$_1$ representing N-methyl-(4R)-4-[(E)-2-butenyl]-4-methyl-L-threonine or MeBmt and its structural derivatives as defined above. When an alkyl group such as a methyl group Me or an ethyl group Et appears before the abbreviation of an amino acid, this means that such an alkyl group is fixed on the amino group of said amino acid residue.

An advantage of the compounds according to the present invention may lie in the impact of an ester bond within macro cyclic backbone in comparison to the regular cyclic amide backbone of the corresponding cycloundecapeptide compounds described in the prior art. Without being bound to theory, it is believed that the replacement of an amide by an ester bond between amino-acid AXX$_7$ in position 7 and D-HIV in position 8 results in a strong effect upon the conformational and physico-chemical properties such as increased conformational flexibility (in P. J. Flory, Statistical $$\text{Cyclo-(AXX}_1\text{-AXX}_2\text{-AXX}_3\text{-AXX}_4\text{-AXX}_5\text{-AXX}_6\text{-AXX}_7\text{-D-Hiv-MeLeu-Leu-MeVal)} \quad \text{(I)}$$

$$1 \quad 2 \quad 3 \quad 4 \quad 5 \quad 6 \quad 7 \quad 8 \quad 9 \quad 10 \quad 11$$

Mechanics of Chain Molecules, Hanser Publishers, NY, 1988) and lipophilicity as well as the absence of a hydrogen donor bond.

It is believed that these structural features transform to pronounced differences in the physico-chemical, pharmacokinetic and biological properties of the compounds of invention compared to the class of CsA derived analogues. A possible rational for the observed higher tolerance to amino acid substitutions in systematic SAR studies may reside in an increase of the conformational space with respect to the bioactive conformation (V. Mikol et al., J. Mol. Biol. (1998) 283, 451-461).

In contrast to cycloundecapeptide analogues of the prior art, single or multiple replacements at positions in fragment between amino-acid in position 2 and amino-acid in position 7 of the natural cycloundecadepsipeptide, as obtained either from U.S. Pat. No. 5,116,816, Example 2, or from WO 02/092033, Example 4, Step 4-1, result in the retention of high binding capacities to Cyclophilin as evidenced by the list of compounds meeting the criteria of the present invention. Most notably, an increase in the binding affinities to Cyp A of factors up to 2-4 for the compounds of the invention compared to compound according to WO 2006/038088 i.e. [D-MeAla]$^3$[EtVal]$^4$-CsA (Debio 025) has been observed.

Apart from the improved active profile (see Examples 5 and 6), the new class of compounds also offers an improved preparation process, especially at an industrial scale.

The invention also encompasses chemical modifications of the compounds of formula I to prolong their circulating lifetimes. Examples of suitable poly(ethylene glycol) derivatives that possess this property are described in e.g. US 2005171328 (NEKTAR THERAPEUTICS AL CORP) or U.S. Pat. No. 6,713,454 (NOBEX CORP).

More preferably, the compounds of the present invention are defined by Formula (I) in which AXX$_1$ is MeBmt, dihydro-MeBmt, 8-hydroxy-MeBmt;
AXX$_2$ is Abu, Val, Thr, Thr(OMe), Thr(OAc), Thr(OCOCH2CH2CH2OH), 5-hydroxy-Nva;
AXX$_3$ is D-MeAla, D-3-fluoro-MeAla, D-MeSer, D-MeSer(OAc), D-MeAsp(OMe);
AXX$_4$ is MeIle, MeMet, MeMet(Ox) with Ox meaning that sulphur atom of methionine is sulphoxyde or sulphone, MeVal, EtVal, EtIle, MeTyr, MeTyr(OAc), MeTyr(OMe), MeThr, MeThr(OtBu), MeThr(OAc), MeThr(OMe), MePhe;
AXX$_5$ is Leu, Val, Ile, Ala;
AXX$_6$ is MeAla, Sar, MeLeu; and
AXX$_7$ is Gly, Ala.

Even more preferably, compounds of Formula (I) are defined in that,

AXX$_1$ is MeBmt, 8-hydroxy-MeBmt;
AXX$_2$ is Abu, Val, Thr, Thr(OMe), Thr(OAc), Thr(OCOCH2CH2CH2OH), 5-hydroxy-Nva;
AXX$_3$ is D-MeAla, D-3-fluoro-MeAla, D-MeSer, D-MeSer(OAc), D-MeAsp(OMe);
AXX$_4$ is MeIle, MeMet, MeMet(Ox) wherein Ox is —SOMe, —SO$_2$Me, MeVal, EtVal, EtIle, MeTyr; and
AXX$_5$ is Leu, Val, Ile
AXX$_6$ is MeAla, Sar, MeLeu; and
AXX$_7$ is Gly, Ala.

In a particular embodiment of the invention, compounds of Formula (I) are defined in that, AXX$_1$ is MeBmt;
AXX$_2$ is Abu, Val, Thr;
AXX$_3$ is D-MeAla;
AXX$_4$ is MeIle, MeVal, EtVal;
AXX$_5$ is Leu, Val, Ile;
AXX$_6$ is MeAla, MeLeu, Sar; and
AXX$_7$ is Gly, Ala.

According to one of the best mode of the invention, compounds of Formula (I) present the following formulae:

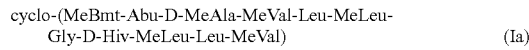 (Ia)

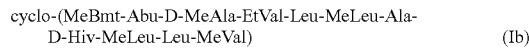 (Ib)

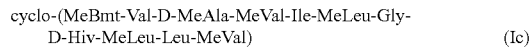 (Ic)

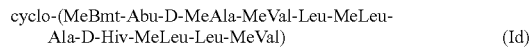 (Id)

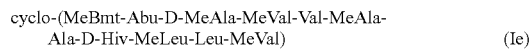 (Ie)

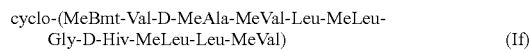 (If)

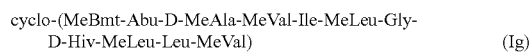 (Ig)

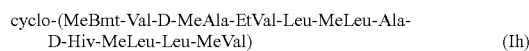 (Ih)

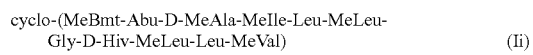 (Ii)

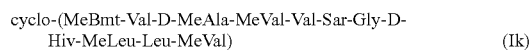 (Ik)

The above listed compounds correspond to an overall optimisation of the most important criteria of the present invention, namely the improvement of the chemical synthesis, the pharmacological properties, the pharmacokinetic and toxicological profiles.

Notably, these compounds demonstrate a much lower potency, as compared to Debio 025, to inhibit hepatic transporters such as MRP2 or OATP1B1. Therefore, these compounds are expected to reduce either the potential adverse effects (e.g. hyperbilirubinemia) or the potential drug-drug interactions (e.g. with HMG-CoA reductase inhibitors such as atorvastatin) related to the inhibition of hepatic transporters, or even both.

Additional compounds of the invention are the followings:

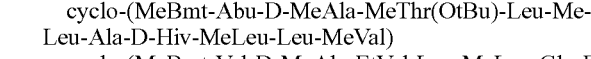
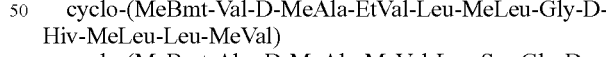
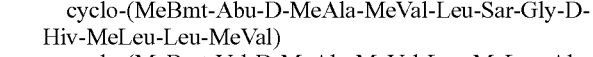
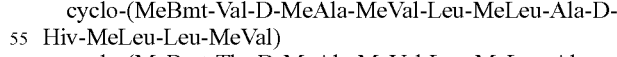
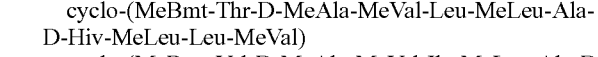
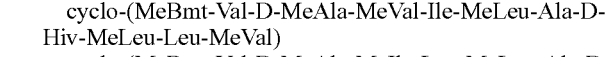
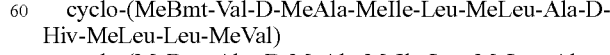
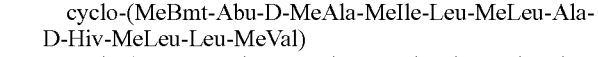
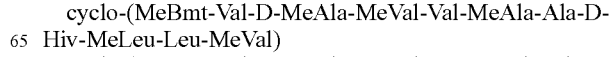
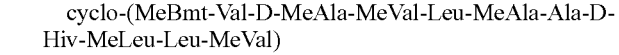

cyclo-(MeBmt-Abu-D-MeAla-MeThr-Leu-MeLeu-Ala-D-Hiv-MeLeu-Leu-MeVal)

cyclo-(MeBmt-Thr(OMe)-D-MeAla-MeVal-Leu-MeLeu-Ala-D-Hiv-MeLeu-Leu-MeVal)

cyclo-(MeBmt-Abu-D-MeAla-EtVal-Leu-MeLeu-Gly-D-Hiv-MeLeu-Leu-MeVal)

cyclo-(MeBmt-Abu-D-MeAla-MeTyr-Leu-MeLeu-Ala-D-Hiv-MeLeu-Leu-MeVal)

cyclo-(MeBmt-Val-D-MeAla-MeVal-Leu-Sar-Gly-D-Hiv-MeLeu-Leu-MeVal)

cyclo-(MeBmt-Thr-D-MeAla-EtVal-Leu-MeLeu-Ala-D-Hiv-MeLeu-Leu-MeVal)

cyclo-(MeBmt-Val-D-MeAla-MeVal-Val-MeLeu-Gly-D-Hiv-MeLeu-Leu-MeVal)

cyclo-(MeBmt-Abu-D-MeAla-MeVal-Ala-MeLeu-Gly-D-Hiv-MeLeu-Leu-MeVal)

cyclo-(MeBmt-Abu-D-MeAla-MeVal-Ile-MeAla-Ala-D-Hiv-MeLeu-Leu-MeVal)

cyclo-(MeBmt-Val-D-MeAla-MeVal-Val-Sar-Gly-D-Hiv-MeLeu-Leu-MeVal)

Other compounds of interests are identified by the following formulae:

cyclo-(MeBmt-Thr(OMe)-D-MeAla-EtVal-Leu-MeLeu-Ala-D-Hiv-MeLeu-Leu-MeVal)

cyclo-((8-hydroxy)MeBmt-Abu-D-MeAla-MeVal-Leu-MeLeu-Ala-D-Hiv-MeLeu-Leu-MeVal)

cyclo-(MeBmt-(5-OH)Nva-D-MeAla-MeVal-Leu-MeLeu-Ala-D-Hiv-MeLeu-Leu-MeVal)

cyclo-(MeBmt-Thr(OR)(R=—COCH$_3$, —COCH$_2$CH$_2$CH$_2$—OH)-D-MeAla-MeVal-Leu-MeLeu-Ala-D-Hiv-MeLeu-Leu-MeVal)

cyclo-(MeBmt-Abu-D-MeAla-MeVal-Val-MeLeu-Ala-D-Hiv-MeLeu-Leu-MeVal)

cyclo-(MeBmt-Val-D-MeSer-MeVal-Leu-MeLeu-Ala-D-Hiv-MeLeu-Leu-MeVal)

cyclo-(MeBmt-Abu-D-MeSer-MeVal-Leu-MeLeu-Ala-D-Hiv-MeLeu-Leu-MeVal)

cyclo-(MeBmt-Abu-D-MeSer(OAc)-MeVal-Leu-MeLeu-Gly-D-Hiv-MeLeu-Leu-MeVal)

cyclo-(MeBmt-Abu-D-MeAsp(OMe)-MeVal-Leu-MeLeu-Gly-D-Hiv-MeLeu-Leu-MeVal)

cyclo-(MeBmt-Val-D-(3-fluoro)MeAla-MeVal-Leu-MeLeu-Gly-D-Hiv-MeLeu-Leu-MeVal)

cyclo-(MeBmt-Abu-D-(3-fluoro)MeAla-MeIle-Leu-MeLeu-Gly-D-Hiv-MeLeu-Leu-MeVal)

cyclo-(MeBmt-Abu-D-MeAla-MeMet-Leu-MeLeu-Gly-D-Hiv-MeLeu-Leu-MeVal)

cyclo-(MeBmt-Abu-D-MeAla-MeMet(Ox)(Ox=—SOMe, —SO$_2$Me)-Leu-MeLeu-Gly-D-Hiv-MeLeu-Leu-MeVal)

cyclo-(MeBmt-Abu-D-MeAla-MePhe-Leu-MeLeu-Gly-D-Hiv-MeLeu-Leu-MeVal)

cyclo-(MeBmt-Abu-D-MeAla-MeTyr(OR)(R=Ac, Me)-Leu-MeLeu-Gly-D-Hiv-MeLeu-Leu-MeVal)

cyclo-(MeBmt-Abu-D-MeAla-MeThr(OR)(R=Me, Ac)-Leu-MeLeu-Ala-D-Hiv-MeLeu-Leu-MeVal)

cyclo-(MeBmt-Abu-D-(3-fluoro)MeAla-EtVal-Leu-MeLeu-Ala-D-Hiv-MeLeu-Leu-MeVal)

cyclo-(MeBmt-Abu-D-MeAla-EtIle-Leu-MeLeu-Ala-D-Hiv-MeLeu-Leu-MeVal)

cyclo-(dihydro)MeBmt-Abu-D-MeAla-MeVal-Leu-MeLeu-Gly-D-Hiv-MeLeu-Leu-MeVal)

cyclo-((8-hydroxy)MeBmt-Abu-D-MeAla-EtVal-Leu-MeLeu-Ala-D-Hiv-MeLeu-Leu-MeVal)

cyclo-((8-hydroxy)MeBmt-Val-D-MeAla-EtVal-Leu-MeLeu-Ala-D-Hiv-MeLeu-Leu-MeVal)

The compounds of the present invention may be obtained by applying classical peptide (solution or solid-phase peptide synthesis; in Houben-Weyl, Methods of Organic Chemistry, Vol. E 22d, Ed.-in-Chief: M. Goodman, Thieme Verlag, Stuttgart, 2003) and organic chemistry or biotechnology, for instance by applying the chemical tools as described by Wenger in Helv. Chim. Acta, 67, 502-25, 1984 or in Helv. Chim. Acta, 66, 2672-702 (1983) and by employing HATU as coupling reagent described in Rich, D. H. et al, Comparative studies of the coupling of N-methylated, sterically hindered amino acids during SPPS, Tetr. Letters. 35, 5981-5984 (1994).

For instance, one of possible general scheme consists to prepare two fragments, namely Fragment A and Fragment B, containing the appropriate residues, with, when necessary the appropriate protective and activating groups, and, in the last steps of the preparation, to link them together to obtain an undecapeptide which is then cyclized to the cycloundecadepsipeptide.

For instance, Fragment (Ax) may be as follows:
H-D-Hiv-MeLeu-Leu-MeVal-AXX$_1$-OH (Ax)
and Fragment (Bx) as follows:
H-AXX$_2$-AXX$_3$-AXX$_4$-AXX$_5$-AXX$_6$-AXX$_7$-OR, (R being an alkyl group) (Bx), then Ax and Bx are coupled to the undecadepsipeptide Ax-Bx, H-D-Hiv-MeLeu-Leu-MeVal-AXX$_1$-AXX$_2$-AXX$_3$-AXX$_4$-AXX$_5$-AXX$_6$-AXX$_7$-OR (R=alkyl,H) and the final stage is the macrolactonisation.

Fragment A, which contains the α-hydroxy acid residue D-Hiv, may be obtained by degradation of a natural cycloundecadepsipeptide (namely Cyclo-(MeBmt-Thr-Sar-MeLeu-Leu-MeLeu-Ala-D-Hiv-MeLeu-Leu-MeVal), the preparation of said cycloundecadepsipeptide being described either in U.S. Pat. No. 5,116,816, Example 2, or in WO 02/092033, Example 4, Step 4-1.

An advantage of the compounds according to the invention versus the prior art lies not only in its active profile (see Examples 5 and 6), but also in its improved preparation process especially at an industrial scale.

1. Starting from the natural compounds (CsA and Cyclo-(MeBmt-Thr-Sar-MeLeu-Leu-MeLeu-Ala-D-Hiv-MeLeu-Leu-MeVal), see FIG. 1, the overall yields for the synthesis of cycloundecadepsipeptide analogues are >50% compared to 20% for DEBIO 025 ([D-MeAla]$^3$-[EtVal]$^4$-CsA as described in WO 2006/038088, DEBIOPHARM SA).

2. The synthesis of the expensive dipeptide derivative Boc-D-MeAla-EtVal-OH (including 4 chemical steps) is not needed. In addition, some of the compounds contain a C-terminal Glycine (Ia, Ic, If, Ig, Ii, Ik), which facilitates the last step of the synthesis (macrolactonisation, no epimerisation).

3. The costs for reagents and starting compounds are considerably lower in case of the compounds according to the invention. Notably, the "reagent of Meerwein" used for the ring opening reaction of CsA is not needed.

4. Fragment B (hexapeptide AXX$_2$-AXX$_7$) can be efficiently obtained by standard solid-phase peptide synthesis using commercially starting compounds (see FIG. 1).

5. In optimizing the preparation of Fragment A from the natural starting compound as well as the condensation (fragment A with fragment B), macrocyclization and final purification steps, the overall yield for obtaining the pharmacologically interesting compounds can amount up to 80%.

6. Overall, the indicated aspects results in a good efficacy and consequently in cost of goods, in particular with respect to the synthesis of the compounds of invention at industrial scale.

The ability of the compounds of the present invention to inhibit replication of HCV was shown in a replicon assay and the essentially absence of immunosuppressive activity was evaluated in a T-cell proliferation assay (see Examples 5 and 6).

A "non immunosuppressive" compound according to the present invention shall be understood as a compound, which is at least 30 fold less immunosuppressive than cyclosporine A (CsA) (determined as the ratio of the $IC_{50}$ (half maximal inhibitory concentration) of the compound to the $IC_{50}$ of Cyclosporin A ($IC_{50}$ compound/$IC_{50}$ CsA)), preferably less than 150 fold, even less than 200 fold and preferably even less than 300 fold. Ideally, the compounds of the invention have a non immunosuppressive activity in vitro of at least 2 log difference with CsA in Concanavalin-A-induced T-Cell proliferation assay.

Accordingly, the compounds of the present invention are considered for use as a medicament, in particular as an antiviral agent, and more specifically for preventing or treating Hepatitis C infections or HCV induced disorders. Hepatitis C infections or HCV induced disorders are e.g. chronic hepatitis, liver cirrhosis or liver cancer, e.g. hepatocellular carcinoma. The compounds of the present invention may also be used for example as a prophylactic treatment of neonates born to HCV infected mothers or of healthcare workers exposed to the virus, or of transplant recipients, e.g. organ or tissue transplant recipients, e.g. liver transplant, to eliminate possible recurrent HCV infection after transplantation.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder.

"Mammal" for purposes of treatment refers to any animal classified as a mammal, including humans, domestic and farm animals or pet animals, such as dogs, horses, cats, cows, monkeys etc. Preferably, the mammal is human.

The term "therapeutically effective amount" refers to an amount of a drug effective to treat a disease or disorder in a mammal.

The compounds of the present invention may be administrated for instance orally to a patient in need, for instance incorporated in a preconcentrated microemultion.

The compounds of the present invention, their pharmaceutically acceptable salts and pro-drugs thereof, where applicable, may be administered in the form of a pharmaceutical composition in which they are in association with a pharmaceutically acceptable adjuvant, diluent or carrier, in order to prevent or treat Hepatitis C infections or HCV induced disorders.

The present invention also provides a pharmaceutical composition comprising a compound of the present invention, or a pharmaceutically acceptable salt thereof, as hereinbefore defined, in association with a pharmaceutically acceptable adjuvant, diluent or carrier. As to the appropriate excipients, diluents and adjuvants, reference may be made to the standard literature describing these, e.g. to chapter 25.2 of Vol. 5 of "Comprehensive Medicinal Chemistry", Pergamon Press 1990, and to "Lexikon der Hilfsstoffe für Pharmazie, Kosmetik and angrenzende Gebiete", by H. P. Fiedler, Editio Cantor, 2002.

The compounds of the present invention may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the compounds of the present invention, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as those used to prepare the medicament LUPRON DEPOT™ (injectable microspheres composed of lactic acid-glycolic acid copolymer and leuprolide acetate), and poly-D-(-)-3-hydroxybutyric acid.

The daily dose of the present invention will necessarily be varied depending upon the host treated, the particular route of administration, and the severity and kind of the illness being treated. Accordingly the optimum dosage may be determined by the practitioner who is treating any particular patient.

The pharmaceutical compositions of the invention may be formulated as creams, gels, solutions, ointments, suspensions or plasters etc. when intended for topical administration; for administration by inhalation, e.g. as aerosols or dry powders; for oral administration, e.g. in the form of tablets, capsules, gels, syrups, suspensions, solutions, powders or granules; for rectal or vaginal administration e.g. as suppositories; or for parenteral injection (including intravenous, subcutaneous, intramuscular, intravascular, or infusion) as a sterile solution, suspension or emulsion.

The active compound of the invention may be administered by any conventional route. It may be administered parentally, e.g., in the form of injectable solutions or suspensions, or in the form of injectable deposit formulations. Preferably, it will be administered orally in the form of solutions or suspensions for drinking, tablets or capsules. Pharmaceutical compositions for oral administration comprising a cycloundecadepsipeptide compound of the invention are described in the Examples. As demonstrated by the examples, such pharmaceutical compositions typically comprise a cycloundecadepsipeptide compound of the invention and one or more pharmaceutically acceptable carrier substances. Typically, these compositions are concentrated and need to be combined with an appropriate diluent, e.g., water, prior to administration. Pharmaceutical compositions for parenteral administration typically also include one or more excipients. Optional excipients include an isotonic agent, a buffer or other pH-controlling agent, and a preservative. These excipients may be added for maintenance of the composition and for the attainment of preferred ranges of pH (about 6.5-7.5) and osmolarity (about 300 mosm/L). Additional examples of formulations for oral administration can be found in U.S. Pat. Nos. 5,525,590 and 5,639,724, and U.S. Pat. Appl. 2003/0104992. By the oral route, the indicated dosage of a cycloundecadepsipeptide compound of the invention for daily to trice weekly administration may be from about 1 mg/kg to about 100 mg/kg, preferably from about 1 mg/kg to about 20 mg/kg. By the intravenous route, the indicated corresponding dosage may be from about 1 mg/kg to about 50 mg/kg, preferably from about 1 mg/kg to about 25 mg/kg. An effective amount of a cycloundecadepsipeptide compound of the invention is understood to be an amount that when administered repeatedly in the course of a therapeutic regimen to a patient in need of treatment of HCV infection results in an objective clinical response such as a statistically significant reduction in serum HCV titer or a significant reduction of serum ALT activity in the patient.

Numerous factors will be taken into consideration by a clinician when determining trial doses for testing efficacy of a pharmaceutical composition comprising a compound of the present invention against HCV infection. Primary among these are the toxicity and half-life of the chosen cycloundecadepsipeptide compound of the invention. Additional factors include the weight of the patient, the age of the patient, the general condition of the patient (including significant systemic or major illnesses including decompensated liver disease, severe preexisting bone marrow compromise and other viral infections), the stage of HCV infection (acute vs. chronic) as indicated, e.g., by serum alanine aminotransferase (ALT) levels, the particular genotype of HCV, previous therapy of HCV infection, the presence of other drugs in the patient, and the like. A course of treatment will require repeated administration of a pharmaceutical composition of the invention. Typically, an adequate drug dose will be administered 3-7 times per week, and duration of treatment may be from about 4 weeks to 6 months, preferably from about 4 weeks to about 12 months. Treatment may be followed by determinations of HCV in serum and measurement of serum ALT levels. The endpoint of treatment is a virological response, i.e., the absence of HCV at the end of a treatment course, several months after initiation of treatment, or several months after completion of treatment. HCV in serum may be measured at the RNA level by methods such as quantitative RT-PCR or northern blots or at the protein level by enzyme immunoassay or enhanced chemiluminescence immunoassay of viral proteins. The endpoint may also include a determination of a serum ALT level in the normal range.

A pharmaceutical composition of the present invention may comprise one or more other ingredients active against HCV infection in addition to the compounds of the present invention such as, for example, another antiviral drug substance, e.g., ribavirin, or an interferon alpha. Compounds of the invention and such other active ingredients can be administered together as part of the same pharmaceutical composition or can be administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and other factors discussed in the previous section. Such additional active ingredients will generally be administered in amounts less than or equal to those for which they are effective as single therapeutic agents. The FDA approved dosages for such active agents that have received FDA approval for administration to humans are publicly available.

The compounds of the invention may be administered as the sole ingredient or together with other drugs, e.g. a drug which has anti-HCV activities, e.g. an interferon, e.g. interferon-alpha-2a or interferon-alpha-2b, e.g. Intron A®, Roferon®, Avonex®, Rebif® or Betaferon®, or an interferon conjugated to a water soluble polymer or to human albumin, e.g. Albuferon® (Human Genome Science), an anti-viral agent, e.g. ribavirin, lamivudine, NV08 or NM283, an inhibitor of the HCV encoded factors like the NS3-4A serine protease, the helicase or RNA polymerase or a prodrug of such an inhibitor, an anti-fibrotic agent, e.g. a N-phenyl-2-pyrimidine-amine derivative, e.g. imatinib, an immune modulating agent, e.g. mycophenolic acid, a salt or a prodrug thereof, e.g. sodium mycophenolate or mycophenolate mofetil, or a S1 P receptor agonist, e.g. FTY720 or an analogue thereof optionally phosphorylated, e.g. as disclosed in EP 627406A1, EP 778263A1, EP 1002792A1, WO 02/18395, WO 02/76995, WO 02/06268, JP2002316985, WO 03/29184, WO 03/29205, WO 03/62252 and WO 03/62248 that are incorporated herein by reference in their entireties.

In specific embodiments, the exemplary interferon used in the present invention is selected from the group consisting of Intron-A®; PEG-Intron®; Roferon®; Pegasys®; Berefor®; Sumiferon®; Wellferon®; Infergen®; Alferon®; Viraferon®; Albuferon® (Human Genome Science); Rebif; Omniferon; Omega and combinations thereof.

Conjugates of interferon to a water-soluble polymer are meant to include especially conjugates to polyalkylene oxide homopolymers such as polyethylene glycol (PEG) or polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used. Such interferon-polymer conjugates are described in U.S. Pat. Nos. 4,766,106; 4,917,888, European Patent Application No. 0 236 987, European Patent Application No. 0 510 356 and international Application Publication No. WO 95/13090. Since the polymeric modification sufficiently reduces antigenic responses, the foreign interferon need not to be completely autologous. Interferon used to prepare polymer conjugates may be prepared from a mammalian extract, such as human, ruminant or bovine interferon, or recombinantly produced. Other forms of interferons include interferon beta, gamma, tau and omega, such as Rebif (Interferon beta 1a) by Serono, Omniferon (natural interferon) by Viragen, or Omega Interferon by Boehringer Ingelheim. Oral interferons such as oral interferon alpha by Amarillo Biosciences. Preferred are conjugates of interferon to polyethylene glycol, also known as pegylated interferons.

Especially preferred conjugates of interferon are pegylated alfa-interferons, for example pegylated interferon-alpha-2a, pegylated interferon-alpha-2b; pegylated consensus interferon or pegylated purified interferon-a product. Pegylated interferon-alpha-2a is described e.g. in European Patent 593,868 and commercially available e.g. under the tradename PEGASYS® (Hoffmann-La Roche). Pegylated interferon-alpha-2b is described, e.g. in European Patent 975,369 and commercially available e.g. under the tradename PEG-INTRON A® (Schering Plough). Pegylated consensus interferon is described in WO 96/11953 (incorporated herein by reference in its entirety). The preferred pegylated alpha-interferons are pegylated interferon-alpha-2a and pegylated interferon-alpha-2b. Also preferred is pegylated consensus interferon.

Daily dosages with respect to the co-agent used will vary depending upon, for example, the compound employed, the host, the mode of administration and the severity of the condition to be treated. For example, lamivudine may be administered at a daily dosage of 100 mg.

The pegylated interferon may be administered parenterally one to three times per week, preferably once a week, at a total weekly dose ranging from 2 to 10 million IU, more preferable 5 to 10 million IU, most preferable 8 to 10 million IU. This may correspond from 0.5 to 2.0 micrograms/kilogram per week on a weekly, three times a week, every other day or daily basis.

In other embodiments, the interferon alpha is a pegylated interferon alpha-2a and the amount of pegylated interferon alpha-2a administered is from 20 to 250 micrograms/kilogram per week on a weekly, three times a week, every other day or daily basis. Preferably, the interferon peg-IFNa2a is administered at an amount of 180 ug once per week.

Antiviral agents typically used for the treatment of HCV are also encompassed in the combination according to the present invention. Such agents include compounds or biologicals that are effective to inhibit the formation and/or replication of a virus in a mammal. This includes agents such as ribavirin (1-beta-D-ribofuranosyl-1H-1,2,4-triazole-3-carboxamide) from Valeant Pharmaceuticals, Inc., Costa Mesa, Calif.; Rebetol® from Schering-Plough Corporation, Kenilworth, N.J., and Copegus® from Hoffmann-La Roche, Nutley, N.J., ribavirin analogues in development such as Levovirin and Viramidine by Valeant, and Mizoribine Monophosphate.

In addition the combination of the present invention may further comprise administration of substrate-based protease inhibitors of HCV NS3-4A serine protease, non-substrate-based NS3 protease inhibitors; phenanthrenequinones, thiazolidines and benzanilides, and the like that have been shown to have activity against HCV infection.

Protease inhibitors for the treatment of HCV are disclosed for example in U.S. Pat. No. 6,004,933 (Spruce et al); U.S. Pat. No. 5,990,276 (Zhang et al); U.S. Pat. No. 5,538,865 (Reyes et al.); WO 02/008251 (Corvas International, Inc.), WO 02/08187 and WO 02/008256 (Schering Corporation); U.S. Pat. Nos. 6,534,523, 6,410,531 and 6,420,380 (Boehringer Ingelheim) and WO 02/060926 (Bristol Myers Squibb); WO 02/48172 and WO 02/18198 (Schering Corporation); WO 02/48157 and WO 02/48116 (Bristol Myers Squibb); WO 98/17679 (Vertex Pharmaceuticals) that are all incorporated herein by reference in their entireties.

Exemplary non-substrate-based NS3 protease inhibitors such as 2,4,6-trihydroxy-3-nitro-benzamide derivatives (Sudo K. et al., Biochemical and Biophysical Research Communications, 1997, 238 643-647; Sudo K. et al. Antiviral Chemistry and Chemotherapy, 1998, 9, 186), including RD3-4082 and RD3-4078; may be used.

Additional experimental agents that have been shown to be efficacious in HCV therapy include HCV NS3-4A serine protease inhibitors BILN 2061 by Boehringer Ingelheim, VX-950 by Vertex, SCH-6, SCH-7, and SCH-351633, by Schering-Plough, and other HCV protease inhibitors in preclinical and clinical development by GlaxoSmithKline, Bristol Myers Squibb, Abbot, Roche, Merck, Pfizer, and Gilead. Additional agents that are currently in clinical development for the treatment of HCV that may be useful in the combination of the invention described herein include TMC 435350 (Tibotec) and ITM-191 (Intermune).

Nucleoside analogs also may be used. An example of one such analog is telbivudine by Idenix (U.S. Pat. No. 6,444,652, U.S. Pat. No. 6,596,700, and WO0196353). Nucleoside or non-nucleoside inhibitors of HCV NS5B RNA-dependent RNA polymerase, such as 2'-C-methyl-3'-O-L-valine ester ribofuranosyl cytidine (NM283, Idenix) as disclosed in WO 2004/002422 also may be used. Branched nucleosides as disclosed in WO 01/90121 and WO 01/92282 (Idenix Pharmaceuticals) may also be used. The contents of these international patent applications are incorporated herein by reference in their entireties.

Additional therapeutic compounds may include antisense molecules directed against HCV genome or an antisense sequence complementary to any part of the HCV genome which increases effectiveness of therapy.

Also contemplated are inhibitors of other targets in the HCV life cycle such as Celgosivir (MBI 3253), a glycoprotein processing inhibitor by Migenix, fusion inhibitor by Trimeris, ACH-0137171 by Achillion. Receptor agonists such as toll like receptor ("TLR") agonists include ANA245, ANA971, ANA975 (U.S. Pat. Nos. 5,041,426, 4,880,784) by Anadys; CpG-10101 a TLR-9 agonist (Coley Pharmaceuticals); an IMPDH inhibitor, mycophenolic acid, a salt or a prodrug thereof sodium mycophenolate or mycophenolate mofetil, or Merimebodib (VX-497, by Vertex); thymosin alpha-1 (Zadaxin or its combination, by SciClone); SCV-07 (SciClone), Belerofon (improved IFN-α by Nautilus); CIVACIR (hepatitis C Immune Globulin) by NABI, or a S1 P receptor agonist, e.g. FTY720 or analogue thereof optionally phosphorylated, e.g. as disclosed in EP 627406A1, EP 778263A1, EP 1002792A1, WO 02/18395, WO 02/76995, WO 02/06268, JP2002316985, WO 03/29184, WO 03/29205, WO 03/62252 and WO 03/62248, the disclosures of which are incorporated herein by reference in their entireties; Resiquimod [VML 600] by 3M Pharmaceuticals, an imiquimod analogue that is a potent inducer of interferon-α and other cytokines. In addition, the compounds of the present invention may be used in combination with Interleukin-10 (Schering-Plough), AMANTADINE (Symmetrel) by Endo Labs Solvay, caspase inhibitor IDN-6556 by Idun Pharma, HCV/MF59 by Chiron, CEPLENE (histamine dichloride) by Maxim, IDN-6556 by Idun PHARM, T67, a beta-tubulin inhibitor by Tularik, FK788 by Fujisawa Healthcare, IdBI 016 (Siliphos, oral silybin-phosphatidyl choline phytosome), Dication by Immtech, hemopurifier by Aethlon Medical, UT 231 B by United Therapeutics; HepeX-C SM1, PPVO-Bay55-8800 (Parapoxvirus ovis) by Bayer; Refanalin (HGF mimetic) by Angion, R803 (Rigel), JTK-003, JTK-002, and JTK-109 (all from Japan Tobacco), HCV-086 (ViroPharma/Wyeth), ISIS-14803 (ISIS Pharmaceuticals), GS-9132 (a polymerase inhibitor by Achillion pharmaceuticals), HCV-793 (Pharmasset and Roche), R1626 (Roche).

Other compounds of interest include Ursodiol (EP 00269516, Axcan Pharma), HE-2000 (a DHEA analog, Colthurst Ltd), EHC-18 (an immunomodulator, Enzo biochem), histamine dihydrochloride (an H2 agonist, WO09104037, Estero-Anstalt), nitazoxanide (Romark), 1-amino-alkylcyclohexanes (U.S. Pat. No. 6,034,134), alkyl lipids (U.S. Pat. No. 5,922,757), vitamin E and other antioxidants (U.S. Pat. No. 5,922,757), bile acids (U.S. Pat. No. 5,846,964), N-(phosphonoacetyl)-L-aspartic acid) U.S. Pat. No. 5,830,905), benzenedicarboxamides (U.S. Pat. No. 5,633,388), polyadenylic acid derivatives (U.S. Pat. No. 5,496,546), 2'3'-dideoxyinosine (U.S. Pat. No. 5,026,687), benzimidazoles (U.S. Pat. No. 5,891,874), plant extracts (U.S. Pat. No. 5,837,257; U.S. Pat. No. 5,725,859 and U.S. Pat. No. 6,056,961) and piperidines (U.S. Pat. No. 5,830,905); N-(phosphonoacetyl)-L-aspartic acid, benzenedicarboxamides, polyadenylic acid derivatives, glycosylation inhibitors, and nonspecific cytoprotective agents that block cell injury caused by the virus infection.

The compounds according to the invention may also be employed in combination with a vaccine or antibody-based approaches to HCV treatment. Therapeutic vaccines include vaccines by Intercell (Therapeutic peptide vaccine IC41 HCV), Epimmune/Genecor, Merix, Tripep (Chiron-VacC), immunotherapy (Therapore) by Avant, T cell therapy by CellExSys, monoclonal antibody XTL-002 by STL, ANA 246 and ANA 246 by Anadys, a therapeutic vaccine directed to E2 by Innogenetics, mAb against E2 envelope protein by XTL Bio, GI-5005 (GlobeImmune Inc), InnoVac-C (WO 9967285, Innogenetics), IC-41 (Intercell), interferon alfa-n3 (Interferon Sciences).

In accordance with the foregoing the present invention provides in a yet further aspect, a pharmaceutical combination comprising at least a) a first agent consisting of the compound of the invention or the pharmaceutical composition according to the present invention, and b) a second agent having the properties to act against HCV replication.

In particular, this pharmaceutical combination is for use in the prevention or treatment of Hepatitis C infections or HCV induced disorders.

Also encompassed is a method for preventing or treating Hepatitis C infections or HCV induced disorders in a subject in need thereof, comprising administering to said subject a therapeutically effective amount of the compound of the invention or the pharmaceutical composition of the invention.

In addition it is provided a method for inhibiting HCV replication in a patient in need thereof, comprising administering to said subject a therapeutically effective amount of the compound of the invention or the pharmaceutical composition of the invention.

Another object of the invention is a method, comprising co-administration concomitantly or in sequence of a therapeutically effective amount of the compound according to the invention or the pharmaceutical composition of the invention and a co-agent selected from an agent having anti-HCV properties.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The administration of a pharmaceutical combination of the invention results in a beneficial effect, e.g. a synergistic therapeutic effect, compared to a monotherapy applying only one of its pharmaceutical active ingredients. A preferred synergistic combination is a combination of the cycloundecadepsipeptide compound of the invention with an interferon, optionally conjugated to a polymer.

A further preferred combination is a combination of compounds of formula I according to the invention with mycophenolic acid, a salt or a prodrug thereof, or with a S1 P receptor agonist, e.g. FTY720.

All patents, patent applications and publications cited herein shall be considered to have been incorporated by reference in their entireties.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1a

Preparation of cycloundecadepsipeptide (Ia): Cyclo-(MeBmt-Abu-D-MeAla-MeVal-Leu-MeLeu-Gly-D-Hiv-MeLeu-Leu-MeVal) (Ia)

1. Preparation of Fragment (Aa), starting from natural cycloundecadepsipeptide Cyclo-(MeBmt-Thr-Sar-MeLeu-Leu-MeLeu-Ala-D-Hiv-MeLeu-Leu-MeVal) (see U.S. Pat. No. 5,116,816, Example 2, or in WO 02/092033), Example 4, Step 4-1)
H-D-Hiv-MeLeu-Leu-MeVal-MeBmt-OH (Aa)
 1.1 Variant A
Preparation of Cyclo-(MeBmt-Thr(O—(N-Imidazolyl)carbonyl)-Sar-MeLeu-Leu-MeLeu-Ala-D-Hiv-MeLeu-Leu-MeVal) (1A).

A solution of Cyclo-(MeBmt-Thr-Sar-MeLeu-Leu-MeLeu-Ala-D-Hiv-MeLeu-Leu-MeVal) (U.S. Pat. No. 5,116,816, Example 2, or in WO 02/092033, Example 4, Step 4-1) (3.00 g, 2.40 mmol, 1.0 equiv.) and 1,1'-carbonyldiimidazole (1.17 g, 7.21 mmol, 3.0 equiv.) in 15 mL of anhydrous $CH_2Cl_2$ was stirred at room temperature for 2.5 h. Progress of the reaction was monitored by analytical UPLC. 81.1% conversion was obtained. Additional amount of 1,1'-carbonyldiimidazole (0.39 g, 2.40 mmol, 1.0 equiv.) was added to the reaction mixture. After additional stirring for 16 h, a 98.8% conversion was obtained. The solution was evaporated under reduced pressure. The residue was dissolved in AcOEt (45 mL) and washed successively with 10% citric acid (45 mL) and brine (45 mL). The organic phase was dried over $Na_2SO_4$, filtered and evaporated under reduced pressure to give a mixture of two compounds (1A) and (2A) as a white powder
UPLC-ESI-MS (m/z): (1A): 1342.75 $[M+H]^+$ ($[C_{68}H_{117}N_{12}O_{15}]^+$, calc. 1342.73), (2A): 1274.77 $[M+H]^+$ ($[C_{65}H_{113}N_{10}O_{15}]^+$; calc. 1274.65)
Preparation of Cyclo-(MeBmt-Thr(O,N-carbonyl)-Sar-MeLeu-Leu-MeLeu-Ala-D-Hiv-MeLeu-Leu-MeVal) (2A).

A solution of compound (1A) as obtained in the preceding reaction (3.41 g, 2.40 mmol) in dry DMSO (15 mL) was stirred and heated at 100° C. for 2 h under argon atmosphere. Progress of the reaction was monitored by analytical UPLC. Full conversion was obtained. Subsequently, the solution was dissolved in AcOEt (45 mL) and washed successively with HCl 1M (30 mL) and 23.2% aq. NaCl solution (15 mL) then 11.6% aq. NaCl solution (45 mL). The organic phase was dried over $Na_2SO_4$, filtered and evaporated under reduced pressure to give the cycloundecadepsipeptide Cyclo-(MeBmt-Thr(O,N-carbonyl)-Sar-MeLeu-Leu-MeLeu-Ala-D-Hiv-MeLeu-Leu-MeVal) (2A) as white powder UPLC-ESI-MS (m/z): 1274.65 $[M+H]^+$ ($[C_{65}H_{113}N_{10}O_{15}]^+$; calc. 1274.65.
Preparation of H-D-Hiv-MeLeu-Leu-MeVal-MeBmt-OMe (fragment (Aa) methyl ester (3A).

To a solution of the cyclodepsipeptide as obtained in the preceding reaction (1.00 g, 0.78 mmol) in 30 mL of MeOH (dry), cooled at 0° C., was added $Ca(OMe)_2$ (0.24 g, 2.35 mmol) in one portion, under argon. After 5 h at 0° C. then 1 h at room temperature, a control of the reaction advancement by UPLC indicates 98.6% conversion. The solution was cooled at 0° C. then neutralized with an aq. solution of 10% citric acid. Methanol was evaporated. The aq. mixture was poured into 100 mL of a mixture of AcOEt/NaCl 23.2% (1:1 v/v). The organic phase was dried over $Na_2SO_4$, filtered and evaporated under reduced pressure. Crude mixture was separated by column chromatography; to give the pentapeptide -D-Hiv-MeLeu-Leu-MeVal-MeBmt-OMe (3A UPLC-ESI-MS (m/z): 669.16 [M+H]$^+$ ([$C_{35}H_{65}N_4O_8$]$^+$; calc. 669.48).

Preparation of Fragment (Aa) H-D-Hiv-MeLeu-Leu-MeVal-MeBmt-OH (4)

A solution of the pentapeptide as obtained in the preceding reaction (3A) (1.15 g, 1.72 mmol, 1.0 equiv.) in THF (8.6 mL) and water (1.1 mL) was cooled to 0° C. in an ice-water bath, then 2 M LiOH (1.72 mL, 3.44 mmol, 2.0 equiv.) was added within 20 seconds. The cooling bath was then removed and the mixture (pH=12-13) was stirred at room temperature for about 3 h. A control of the reaction advancement by UPLC indicates a full conversion Subsequently, the solution was cooled to 0° C. and neutralized with 10% citric acid. Tetrahydrofurane was evaporated under reduced pressure. The residue was dissolved in AcOEt (50 mL) and washed with 10% citric acid (3 mL) and 23.2% aq. NaCl solution (50 mL) (pH 3). The organic phase was dried over $Na_2SO_4$, filtered and evaporated under reduced pressure to give Fragment (Aa) H-D-Hiv-MeLeu-Leu-MeVal-MeBmt-OH (4) as a white powder UPLC-ESI-MS (m/z) 655.21 [M+H]$^+$ ([$C_{34}H_{63}N_4O_8$]$^+$; calc. 655.46).

1.2 Variant B

Preparation of H-D-Hiv-MeLeu-Leu-MeVal-MeBmt-Thr-Sar-MeLeu-Leu-MeLeu-Ala-OMe

To a solution of the natural Cyclo-(MeBmt-Thr-Sar-MeLeu-Leu-MeLeu-Ala-D-Hiv-MeLeu-Leu-MeVal) (as obtained either from U.S. Pat. No. 5,116,816, Example 2, or from WO 02/092033, Example 4, Step 4-1) (3.0 g, 2.40 mmol) in dry MeOH (90 mL), cooled at 0° C., was added under argon MeONa (0.519 g, 9.6 mmol, 4.0 equiv.). After 1 hour at 0° C. then 2 h at room temperature, a control of the reaction advancement by HPLC indicates the completion. The solution was cooled at 0° C. then neutralized (pH 5-6) with an aq. solution of 10% citric acid. Methanol was evaporated. The aqueous mixture was poured into 150 mL of ethyl acetate. The organic layer was washed with $H_2O$ (20 mL) and brine (20 mL) and dried over $MgSO_4$, filtered. Solvent evaporation in vacuo and flash chromatography on silica gel gave pure H-D-Hiv-MeLeu-Leu-MeVal-MeBmt-Thr-Sar-MeLeu-Leu-MeLeu-Ala-OMe Preparation of H-D-Hiv(O—(N-imidazolyl)carbonyl)-MeLeu-Leu-MeVal-MeBmt-Thr(O—(N-imidazolyl)carbonyl)-Sar-MeLeu-Leu-MeLeu-Ala-OMe (1B)

A solution of the undecapeptide as obtained in the preceding reaction (2.96 g, 2.31 mmol, 1.0 equiv.) and 1,1'-carbonyldiimidazole (1.50 g, 9.25 mmol, 4.0 equiv.) in 53 mL of anhydrous $CH_2Cl_2$ was stirred at room temperature for 22 h. Progress of the reaction was monitored by analytical HPLC and TLC. The solution was evaporated under reduced pressure. The residue was dissolved in 150 mL of ethyl acetate and washed successively with 10% citric acid (30 mL), $H_2O$ (30 mL) and brine (30 mL). The organic phase was dried over $Na_2SO_4$, filtered and evaporated under reduced pressure. The crude product was purified by flash chromatography to give H-D-Hiv(O—(N-imidazolyl)carbonyl)-MeLeu-Leu-MeVal-MeBmt-Thr(O—(N-imidazolyl)carbonyl)-Sar-MeLeu-Leu-MeLeu-Ala-OMe (1B) as a white powder.

Preparation of H-D-Hiv(O—(N-imidazolyl)carbonyl)-MeLeu-Leu-MeVal-MeBmt-Thr(O,N-carbonyl)-Sar-MeLeu-Leu-MeLeu-Ala-OMe (2B)

A solution of the undecapeptide as obtained in the preceding reaction (3.26 g, 2.22 mmol) in dry DMSO (40 mL) was stirred and heated at 100° C. for 3.5 h under argon atmosphere. Progress of the reaction was monitored by TLC and analytical HPLC. Subsequently, the solution was dissolved in AcOEt (200 mL) and washed successively with aq. 10% citric acid (2 times, 30 mL), $H_2O$ (1×30 mL) and sat. aq. NaCl solution (1×30 mL). The organic phase was dried over $Na_2SO_4$, filtered and evaporated under reduced pressure. The crude product was purified by flash chromatography. The residue after solvents evaporation was dried in high vacuum to give the undecapeptide H-D-Hiv(O—(N-imidazolyl)carbonyl)-MeLeu-Leu-MeVal-MeBmt-Thr(O,N-carbonyl)-Sar-MeLeu-Leu-MeLeu-Ala-OMe (2B) as white powder.

Preparation of H-D-Hiv-MeLeu-Leu-MeVal-MeBmt-OMe (3B)

To a solution of the undecapeptide (2B) as obtained in the preceding reaction (3.05 g, 2.17 mmol) in 100 mL of MeOH (dry), cooled at 0° C., was added MeOK (0.456 g, 6.53 mmol) in one portion, under argon. After 1 h at 0° C. then 1 h at room temperature, a control of the reaction advancement by HPLC indicates the completion. The solution was cooled at 0° C. then neutralized with an aq. solution of 10% citric acid. Methanol was evaporated. The aq. mixture was poured into 100 mL of a mixture of AcOEt/$H_2O$ (1:1 v/v). The organic layer was washed with $H_2O$ (1×10 mL) and brine (1×10 mL). The organic phase was dried over $Na_2SO_4$, filtered and evaporated under reduced pressure. Crude mixture was separated by preparative HPLC to give the pentapeptide H-D-Hiv-MeLeu-Leu-MeVal-MeBmt-OMe (3B).

Preparation of H-D-Hiv-MeLeu-Leu-MeVal-MeBmt-OH (4, Fragment Aa)

A solution of the pentapeptide as obtained in the preceding reaction (1.265 g, 1.88 mmol, 1.0 equiv.) in THF (18.8 mL) was cooled to 0° C. in an ice-water bath, then 0.2 M LiOH (18.8 mL, 3.66 mmol, 2.0 equiv.) was added dropwise over 20 min. The cooling bath was then removed and the mixture (pH=12-13) was stirred at room temperature for about 2.5 h (TLC control). Subsequently, the solution was cooled to 0° C. and neutralized with 0.1 M HCl (pH 2-3). Tetrahydrofuran was evaporated under reduced pressure. The residue was dissolved in AcOEt (100 mL) and washed with 10% citric acid (1×20 mL), $H_2O$ (1×20 mL) and brine (1×20 mL). The organic phase was dried over $Na_2SO_4$, filtered and evaporated under reduced pressure. Crude mixture was separated by CC to give the pentapeptide (sodium salt) H-D-Hiv-MeLeu-Leu-MeVal-MeBmt-ONa as a white powder.

HR-MALDI-MS: 677.46 [M+Na]$^+$ ([$C_{34}H_{62}N_4NaO_8$]$^+$; calc. 677.4465).

2. Preparation of Fragment (Ba)

H-Abu-D-MeAla-MeVal-Leu-MeLeu-Gly-OMe (Ba)

2.1. Preparation of Boc-MeLeu-Gly-OMe

To a solution of commercially available H-Gly-OMe.HCl (4.0 g, 31.8 mmol, 1.0 equiv.) in dry DCM (240 mL), cooled at 0° C., was added under argon DIPEA (32.88 mL, 189.0 mmol, 6.0 equiv.). Subsequently, after 15 min, HATU (15.72 g, 41.34 mmol, 1.3 equiv.) and Boc-MeLeu-OH (7.8 g, 31.8 mmol, 1.0 equiv.) were added in one portion. After 15 min at 0° C. then 22.45 h at room temperature, a control of the reaction advancement by TLC indicates the completion. The reaction was quenched by addition of 10% $NaHCO_3$ (40 mL) and stirred 15 min. Reaction mixture was diluted with DCM (400 mL) and washed with 10% citric acid (1×80 mL), $H_2O$ (1×80 mL) and brine (1×80 mL). The organic phase was dried over $Na_2SO_4$, filtered and evaporated under reduced pressure. The crude mixture was separated to give the ester Boc-MeLeu-Gly-OMe as a white oily foam UPLC-ESI-MS (m/z) 339.0234 [M+Na]$^+$ ([$C_{15}H_{28}N_2NaO_5$]$^+$; calc. 339.1896).

2.2. Preparation of H-MeLeu-Gly-OMe

A solution of the dipeptide, as obtained in the preceding reaction, (9.9 g, 31.29 mmol, 1.0 equiv.) in TFA/DCM (30 mL, 2:3 v/v) was kept at 0° C. for 45 min and 2 h at room temp., and the solvents removed under reduced pressure. The crude product was dried under high vacuum (20 min). Subsequently, DCM (60 mL) was added and the mixture was triturated at 0° C. with DIPEA (2.0 mL) to pH 7-8 to neutralize an excess of TFA. After evaporation and drying the crude amine salt of the dipeptide H-MeLeu-Gly-OMe was used to the next coupling step without further purification.

UPLC-ESI-MS (m/z) 217.0546 [M+H]$^+$ ([$C_{10}H_{21}N_2O_3$]$^+$; calc. 217.1552).

2.3. Preparation of Boc-Leu-MeLeu-Gly-OMe

To a solution of the dipeptide, as obtained in the preceding reaction, (3.38 g, 15.63 mmol, 1.0 equiv.) in dry DCM (160 mL), cooled at 0° C., was added under argon DIPEA (8.08 mL, 46.89 mmol, 3.0 equiv.). Subsequently, after 10 min, HATU (7.72 g, 20.14 mmol, 1.3 equiv.) and Boc-Leu-OH (3.98 g, 17.19 mmol, 1.1 equiv.) were added in one portion. After 15 min at 0° C. then 15.45 h at room temperature a control of the reaction advancement by TLC indicates the completion. The reaction was quenched by addition of 10% NaHCO$_3$ (36 mL) and stirred 15 min. Reaction mixture was diluted with DCM (240 mL) and washed with 10% citric acid (1×60 mL), H$_2$O (1×60 mL) and brine (1×60 mL). The organic phase was dried over Na$_2$SO$_4$, filtered and evaporated under reduced pressure. The crude mixture was separated by CC to give the ester Boc-Leu-MeLeu-Gly-OMe as a yellowish oil UPLC-ESI-MS (m/z) 430.0120 [M+H]$^+$ ([$C_{21}H_{40}N_3O_6$]$^+$; calc. 430.2917).

2.4. Preparation of H-Leu-MeLeu-Gly-OMe

A solution of the tripeptide, as obtained in the preceding reaction, (3.0 g, 6.98 mmol, 1.0 equiv.) in TFA/DCM (12 mL, 1:1 v/v) was kept at 0° C. for 1 h and 2 h at room temp., and the solvents removed under reduced pressure. The crude product was dried under high vacuum (15 min). Subsequently, DCM (20 mL) was added and the mixture was triturated at 0° C. with DIPEA to pH 7-8 to neutralize an excess of TFA. After evaporation and drying the crude amine salt of H-Leu-MeLeu-Gly-OMe was used to the next coupling step without further purification.

UPLC-ESI-MS (m/z) 330.0227 [M+H]$^+$ ([$C_{16}H_{32}N_3O_4$]$^+$; calc. 330.2393); 352.0016 [M+Na]$^+$ ([$C_{16}H_{31}N_3NaO_4$]$^+$; calc. 352.4248); 659.1626 [2M+H]$^+$ ([$C_{32}H_{63}N_6O_8$]$^+$; calc. 659.1626).

2.5. Preparation of Boc-MeVal-Leu-MeLeu-Gly-OMe

To a solution of the tripeptide, as obtained in the preceding reaction, (2.3 g, 6.98 mmol, 1.0 equiv.) in dry DCM (105 mL), cooled at 0° C., was added under argon DIPEA (3.61 mL, 20.34 mmol, 3.0 equiv.). Subsequently, after 10 min, HATU (3.45 g, 9.07 mmol, 1.3 equiv.) and Boc-MeVal-OH (1.78 g, 7.68 mmol, 1.1 equiv.) were added in one portion. After 15 min at 0° C. then 15.45 h at room temperature a control of the reaction advancement by TLC indicates the completion. The reaction was quenched by addition of 10% NaHCO$_3$ (25 mL) and stirred 15 min. Reaction mixture was diluted with DCM (150 mL) and washed with 10% citric acid (1×50 mL), H$_2$O (1×50 mL) and brine (1×50 mL). The organic phase was dried over Na$_2$SO$_4$, filtered and evaporated under reduced pressure. The crude mixture was separated by to give the ester Boc-MeVal-Leu-MeLeu-Gly-OMe as a yellowish oil UPLC-ESI-MS (m/z) 543.0484 [M+H]$^+$ ([$C_{27}H_{51}N_4O_7$]$^+$; calc. 543.3758); 565.0467 [M+Na]$^+$ ([$C_{27}H_{50}N_4NaO_7$]$^+$; calc. 565.3577).

2.6. Preparation of H-MeVal-Leu-MeLeu-Gly-OMe

A solution of the tetrapeptide, as obtained in the preceding reaction, (3.56 g, 6.56 mmol, 1.0 equiv.) in TFA/DCM (12 mL, 1:1 v/v) was kept at 0° C. for 1 h and 2 h at room temp., and the solvents removed under reduced pressure. The crude product was dried under high vacuum (about 15 min). Subsequently, DCM (45 mL) was added and the mixture was triturated at 0° C. with DIPEA to pH 7-8 to neutralize an excess of TFA. After evaporation and drying the crude amine salt of the tetrapeptide H-MeVal-Leu-MeLeu-Gly-OMe was used to the next coupling step without further purification.

UPLC-ESI-MS (m/z) 443.0694 [M+H]$^+$ ([$C_{22}H_{43}N_4O_5$]$^+$; calc. 443.3233); 465.0063 [M+Na]$^+$ ([$C_{22}H_{42}N_4NaO_5$]$^+$; calc. 465.3053).

2.7. Preparation of Boc-D-MeAla-MeVal-Leu-MeLeu-Gly-OMe

To a solution of the tetrapeptide, as obtained in the preceding reaction, (2.90 g, 6.56 mmol, 1.0 equiv.) in dry DCM (110 mL), cooled at 0° C., was added under argon DIPEA (3.39 mL, 19.68 mmol, 3.0 equiv.). Subsequently, after 10 min, HATU (3.24 g, 8.53 mmol, 1.3 equiv.) and Boc-D-MeAla-OH (1.46 g, 7.21 mmol, 1.1 equiv.) were added in one portion. After 15 min at 0° C. then 17.45 h at room temperature a control of the reaction advancement by TLC indicates the completion. The reaction was quenched by addition of 10% NaHCO$_3$ (25 mL) and stirred 15 min. Reaction mixture was diluted with DCM (150 mL) and washed with 10% citric acid (1×50 mL), H$_2$O (1×50 mL) and brine (1×50 mL). The organic phase was dried over Na$_2$SO$_4$, filtered and evaporated under reduced pressure. The crude mixture was separated by CC to give the ester Boc-D-MeAla-MeVal-Leu-MeLeu-Gly-OMe as a yellowish foam UPLC-ESI-MS (m/z) 628.56 [M+H]$^+$ ([$C_{31}H_{58}N_5O_8$]$^+$; calc. 628.4285); 650.53 [M+Na]$^+$ ([$C_{31}H_{57}N_5NaO_8$]$^+$; calc. 650.4105).

2.8. Preparation of H-D-MeAla-MeVal-Leu-MeLeu-Gly-OMe

A solution of the pentapeptide, as obtained in the preceding reaction, (1.6 g, 2.55 mmol, 1.0 equiv.) in TFA/DCM (6 mL, 1:1 v/v) was kept at 0° C. for 1 h and 2 h at room temp., and the solvents removed under reduced pressure. The crude product was dried under high vacuum (about 15 min). Subsequently, DCM (20 mL) was added and the mixture was triturated at 0° C. with DIPEA to pH 7-8 to neutralize an excess of TFA. After evaporation and drying the crude amine salt of the pentapeptide H-D-MeAla-MeVal-Leu-MeLeu-Gly-OMe was used to the next coupling step without further purification.

UPLC-ESI-MS (m/z) 528.49 [M+H]$^+$ ([$C_{26}H_{50}N_5O_6$]$^+$; calc. 528.3761).

2.9. Preparation of Boc-Abu-D-MeAla-MeVal-Leu-MeLeu-Gly-OMe

To a solution of the pentapeptide, as obtained in the preceding reaction, (1.33 g, 2.52 mmol, 1.0 equiv.) in dry DCM (60 mL), cooled at 0° C., was added under argon DIPEA (1.30 mL, 7.56 mmol, 3.0 equiv.). Subsequently, after 10 min, HATU (1.25 g, 3.28 mmol, 1.3 equiv.) and Boc-Abu-OH (0.56 g, 2.77 mmol, 1.1 equiv.) were added in one portion. After 15 min at 0° C. then over night at room temperature a control of the reaction advancement by TLC indicates the completion. The reaction was quenched by addition of 10% NaHCO$_3$ (15 mL) and stirred 15 min. Reaction mixture was diluted with DCM (100 mL) and washed with 10% citric acid (1×40 mL), H$_2$O (1×40 mL) and brine (1×40 mL). The organic phase was dried over Na$_2$SO$_4$, filtered and evaporated under reduced pressure. The crude mixture was separated by CC to give the ester Boc-Abu-D-MeAla-MeVal-Leu-MeLeu-Gly-OMe as a yellowish foam UPLC-ESI-MS (m/z) 713.1513 [M+H]$^+$ ([$C_{35}H_{65}N_6O_9$]$^+$; calc. 713.4813); 735.1010 [M+Na]$^+$ ([$C_{35}H_{64}N_6NaO_9$]$^+$; calc. 735.4632).

2.10. Preparation of H-Abu-D-MeAla-MeVal-Leu-MeLeu-Gly-OMe (Ba)

A solution of the hexapeptide, as obtained in the preceding reaction, (0.82 g, 1.15 mmol, 1.0 equiv.) in TFA/DCM (6 mL, 1:1 v/v) was kept at 0° C. for 1 h and 1 h at room temp., and the solvents removed under reduced pressure. The crude product was dried under high vacuum (about 15 min). Subsequently, DCM (25 mL) was added and the mixture was triturated at 0° C. with DIPEA to pH 7-8 to neutralize an excess of TFA. After evaporation and drying the crude amine salt of the hexapeptide H-Abu-D-MeAla-MeVal-Leu-MeLeu-Gly-OMe was used to the next coupling step without further purification.

UPLC-ESI-MS (m/z) 613.1925 [M+H]$^+$ ([$C_{30}H_{57}N_6O_7$]$^+$; calc. 613.4289).

3. Coupling of Fragment (Aa) and Fragment (Ba)

3.1. Preparation of D-Hiv-MeLeu-Leu-MeVal-MeBmt-Abu-D-MeAla-MeVal-Leu-MeLeu-Gly-OMe To a solution of the hexapeptide H-Abu-D-MeAla-MeVal-Leu-MeLeu-Gly-OMe, as obtained in the preceding reaction, (0.7 g, 1.14 mmol, 1.0 equiv.) in dry DCM (33 mL), cooled at 0° C., was added under argon DIPEA (0.59 mL, 3.42 mmol, 3.0 equiv.). Subsequently, after 10 min, HATU (0.56 g, 1.48 mmol, 1.3 equiv.) and pentapeptide D-Hiv-MeLeu-Leu-MeVal-MeBmt-OH (0.75 g, 1.14 mmol, 1.0 equiv.) were added in one portion. After 15 min at 0° C. then 16.45 h at room temperature, a control of the reaction advancement by TLC indicates the completion. The reaction was quenched by addition of 10% NaHCO$_3$ (10 mL) and stirred 15 min. Reaction mixture was diluted with DCM (130 mL) and washed with 10% citric acid (1×35 mL), H$_2$O (1×35 mL) and brine (1×35 mL). The organic phase was dried over Na$_2$SO$_4$, filtered and evaporated under reduced pressure. The crude product was purified by CC to give the undecapeptide D-Hiv-MeLeu-Leu-MeVal-MeBmt-Abu-D-MeAla-MeVal-Leu-MeLeu-Gly-OMe as a white foam UPLC-ESI-MS (m/z) 625.6903 [M/2+H]$^+$ ([$C_{32}H_{59}N_5O_7$]$^+$; calc. 625.4415); 1249.7793 [M+H]$^+$ ([$C_{64}H_{117}N_{10}O_{14}$]$^+$; calc. 1249.8751).

3.2. Preparation of D-Hiv-MeLeu-Leu-MeVal-MeBmt-Abu-D-MeAla-MeVal-Leu-MeLeu-Gly-OH A solution of the undecadepsipeptide, as obtained in the preceding reaction, (1.30 g, 1.04 mmol, 1.0 equiv.) in THF (10.4 mL) was cooled to 0° C. in an ice-water bath, then 0.2 M LiOH (10.4 mL, 2.08 mmol, 2.0 equiv.) was added dropwise over 10 min. The cooling bath was kept and the mixture (pH=12-13) was stirred at 0° C. for about 20 min and 30 min at rt (TLC control). Subsequently, the solution was cooled to 0° C. and neutralized with an aq. 10% citric acid (pH 3-4). The solution was evaporated under reduced pressure. The residue was dissolved in AcOEt (140 mL) and washed with H$_2$O (1×30 mL) and brine (1×30 mL). The organic phase was dried over Na$_2$SO$_4$, filtered and evaporated under reduced pressure. The crude product was purified by CC to give the undecapeptide D-Hiv-MeLeu-Leu-MeVal-MeBmt-Abu-D-MeAla-MeVal-Leu-MeLeu-Gly-OH as a white powder UPLC-ESI-MS (m/z) 1235.7690 [M+H]$^+$ ([$C_{63}H_{115}N_{10}O_{14}$]$^+$; calc. 1235.8594).

4. Macrolactonisation: Preparation of cyclo-(MeBmt-Abu-D-MeAla-MeVal-Leu-MeLeu-Gly-D-Hiv-MeLeu-Leu-MeVal) (Ia)

To a solution of DMAP (0.507 g, 4.144 mmol, 4.0 equiv.) and benzotriazol-1-yloxytripyrrolidinophosphonium hexafluorophosphate (PyBOP) (1.078 g, 2.071 mmol, 2.0 equiv.) in DCM (128 mL) was added dropwise over 2 h a solution of undecadepsipeptide acid as obtained in the preceding reaction (1.28 g, 1.036 mmol, 1.0 equiv.) in DCM (20 mL). The mixture was stirred overnight (22 h). after the addition of acid was complete; then, the mixture was transferred to a separating funnel. Total reaction time=24 h. The solution was washed with 0.1 M HCl (20 mL) and the organic layer was separated and dried over MgSO$_4$, filtered, and concentrated under reduced pressure. The crude product was purified by CC, thereby giving the cycloundecadepsipeptide cyclo-(MeBmt-Abu-D-MeAla-MeVal-Leu-MeLeu-Gly-D-Hiv-MeLeu-Leu-MeVal) (Ia) as a white solid Subsequently, the obtained compound was repurified by preparative HPLC (to give the cyclo-(MeBmt-Abu-D-MeAla-MeVal-Leu-MeLeu-Gly-D-Hiv-MeLeu-Leu-MeVal) as a white powder. Purity 99.38% (80° C., 30 min).

($C_{63}H_{112}N_{10}O_{13}$, MW=1217.6226 g/mol).

UPLC (40° C., ACQUITY UPLC® BEH C$_{18}$ 1.7 µm, 214 nm, 50→95%, 7 min) t$_R$=2.923 min.

UPLC

The overall yield to obtain the undecadepsipeptide cyclo-(MeBmt-Abu-D-MeAla-MeVal-Leu-MeLeu-Gly-D-Hiv-MeLeu-Leu-MeVal) starting from the natural undecadepsipeptide Cyclo-(MeBmt-Thr-Sar-MeLeu-Leu-MeLeu-Ala-D-Hiv-MeLeu-Leu-MeVal) is above 50%.

Example 1b

Compounds (Ic), (If), (Ig), (Ii) and (Ik) can be prepared according to analogous reaction pathway as Example 1a.

Example 2

Preparation of cycloundecadepsipeptide (Ib): cyclo-(MeBmt-Abu-D-MeAla-EtVal-Leu-MeLeu-Ala-D-Hiv-MeLeu-Leu-MeVal) (Ib)

2. Preparation of Fragment (Bb):

H-Abu-D-MeAla-EtVal-Leu-MeLeu-Ala-OMe (Bb)

2.1. Preparation of Boc-MeLeu-Ala-OMe

To a solution of commercially available H-Ala-OMe.HCl (2.00 g, 14.32 mmol, 1.0 equiv.) in dry DCM (130 mL), cooled at 0° C., was added under argon DIPEA (14.68 mL, 86.0 mmol, 6.0 equiv.). Subsequently, after 15 min, HATU (6.52 g, 17.18 mmol, 1.2 equiv.) and Boc-MeLeu-OH (3.512 g, 14.32 mmol, 1.0 equiv.) were added in one portion. After 15 min at 0° C. then 48 h at room temperature (RT=2 days 15 min), a control of the reaction advancement by TLC indicates the completion. The reaction was quenched by addition of 10% NaHCO$_3$ (20 mL) and stirred 15 min. Reaction mixture was diluted with DCM (200 mL) and washed with 10% citric acid (1×40 mL), H$_2$O (1×40 mL) and brine (1×40 mL). The organic phase was dried over Na$_2$SO$_4$, filtered and evaporated under reduced pressure. Crude mixture was separated by CC to give the ester Boc-MeLeu-Ala-OMe as a pale yellowish oil. The sample (30 mg) was repurified by semi-preparative RP-HPLC and the peptide was lyophilized to give the ester Boc-MeLeu-Ala-OMe as a white powder.

2.2. Preparation of H-MeLeu-Ala-OMe

A solution of dipeptide as obtained in the preceding reaction (1.70 g, 5.14 mmol, 1.0 equiv.) in TFA/DCM (10 mL, 2:3 v/v) was kept at 0° C. for 1.5 h, and the solvents removed under reduced pressure. The crude product was dried under high vacuum (20 min). Subsequently, DCM (10 mL) was added and the mixture was triturated at 0° C. with DIPEA to pH 7-8 to neutralize an excess of TFA. Subsequently, reaction mixture was diluted with DCM (60 mL) and washed with H$_2$O (1×10 mL) and brine (1×10 mL). The organic phase was filtered, dried (Na$_2$SO$_4$), evaporated and dried under high vacuum. The crude amine salt of H-MeLeu-Ala-OMe was used for the next coupling step without further purification.

2.3 Preparation of Boc-Leu-MeLeu-Ala-OMe

To a solution of dipeptide as obtained in the preceding reaction (7) (2.17 g, 9.42 mmol, 1.0 equiv.) in dry DCM (108 mL), cooled at 0° C., was added under argon DIPEA (6.45 mL, 37.68 mmol, 4.0 equiv.). Subsequently, after 10 min, HATU (4.65 g, 12.25 mmol, 1.3 equiv.) and Boc-Leu-OH (2.39 g, 10.36 mmol, 1.1 equiv.) were added in one portion. After 15 min at 0° C. then 15 h at room temperature (15 h 15 min), a control of the reaction advancement by TLC indicates the completion. The reaction was quenched by addition of 10% NaHCO$_3$ (10 mL) and stirred 15 min. Reaction mixture was diluted with DCM (50 mL) and washed with 10% citric acid (1×20 mL), H$_2$O (1×20 mL) and brine (1×20 mL). The organic phase was dried over Na$_2$SO$_4$, filtered and evaporated under reduced pressure. Crude mixture was separated by CC to give the tripeptide Boc-Leu-MeLeu-Ala-OMe as a yellowish oil. The sample was re-purified by semi-preparative RP-HPLC and the peptide lyophilized to give the tripeptide Boc-Leu-MeLeu-Ala-OMe as a white powder.

2.4. Preparation of H-Leu-MeLeu-Ala-OMe

A solution of the tripeptide as obtained in the preceding reaction (2.00 g, 4.50 mmol, 1.0 equiv.) in TFA/DCM (10 mL, 2:3 v/v) was kept at 0° C. for 2 h, and the solvents removed under reduced pressure. The product was dried under high vacuum (20 min) to give the crude material. Subsequently, DCM (20 mL) was added and the mixture was triturated at 0° C. with DIPEA to pH 7-8 (Lackmus-paper) to neutralize an excess of TFA. After evaporation and drying the crude amine H-Leu-MeLeu-Ala-OMe was used to the next coupling step without further purification. The sample (25 mg) was repurified by semi-preparative RP-HPLC and the product was lyophilized to give the tripeptide H-Leu-MeLeu-Ala-OMe as a solid

2.5. Preparation of Boc-D-MeAla-EtVal-OH

Boc-D-MeAla-EtVal-OH was obtained starting from Boc-D-MeAla-Val-OMe using BuLi and Triethyloxoniumfluoroborate, followed by hydrolysis of the methylester according to literature [Jean François. Guichou, PhD thesis entitled "De nouveaux analogues de Cyclosporine A comme agent anti-VIH-1", Faculté des Sciences, Université de Lausanne, 2001, p. 121-122].

2.6. Preparation of Boc-D-MeAla-EtVal-Leu-MeLeu-Ala-OMe

To a solution of the tripeptide H-Leu-MeLeu-Ala-OMe (0.096 g, 0.291 mmol, 1.0 equiv.) in dry DCM (8 mL), cooled at −8° C., was added under argon DIPEA (0.15 mL, 0.87 mmol, 3.0 equiv.). Subsequently, after 10 min, HATU (0.13 g, 0.35 mmol, 1.2 equiv.) and the dipeptide Boc-D-MeAla-EtVal-OH (0.1 g, 0.29 mmol, 1.0 equiv.) were added in one portion. After 10 min at −8° C. then 40 min at room temperature, a control of the reaction advancement by HPLC indicates the completion. The reaction was quenched by addition of 10% NaHCO$_3$ (1 mL) and stirred 15 min. Reaction mixture was diluted with DCM (20 mL) and washed with 10% citric acid (1×5 mL), H$_2$O (1×5 mL) and brine (1×5 mL). The organic phase was dried over Na$_2$SO$_4$, filtered and evaporated under reduced pressure. The crude mixture was separated by CC to give the pentapeptide Boc-D-MeAla-EtVal-Leu-MeLeu-Ala-OMe as an oil. The sample was repurified by semi-preparative RP-HPLC and the product was lyophilized to give the pentapeptide Boc-D-MeAla-EtVal-Leu-MeLeu-Ala-OMe as a white powder.

2.7. Preparation of H-D-MeAla-EtVal-Leu-MeLeu-Ala-OMe

A solution of the pentapeptide as obtained in the preceding reaction (0.45 g, 0.69 mmol, 1.0 equiv.) in TFA/DCM (4.0 mL, 2:3 v/v) was kept at 0° C. for 1.5 h, and the solvents removed under reduced pressure. The residue was dried under high vacuum (0.5 h). Subsequently, DCM (10 mL) was added and the mixture was triturated at 0° C. with DIPEA to pH 7-8 (Lackmus-paper) to neutralize an excess of TFA. After evaporation and drying the crude amine salt of the pentapeptide H-D-MeAla-EtVal-Leu-MeLeu-Ala-OMe was used to the next coupling step without further purification. A sample (30 mg) was purified by semi-preparative RP-HPLC and the peptide was lyophilized to give the free amine of the pentapeptide H-D-MeAla-EtVal-Leu-MeLeu-Ala-OMe as a white powder.

2.8. Preparation of Boc-Abu-D-MeAla-EtVal-Leu-MeLeu-Ala-OMe

To a solution of the crude pentapeptide as obtained in the preceding reaction (0.2 g, 0.36 mmol, 1.0 equiv.) in dry DCM (10 mL), cooled at 0° C., was added under argon DIPEA (0.18 mL, 1.08 mmol, 3.0 equiv.). Subsequently, after 5 min, HATU (0.19 g, 0.5 mmol, 1.4 equiv.) and Boc-Abu-OH (0.088 g, 0.42 mmol, 1.1 equiv.) were added in one portion. After 15 min at 0° C. then 1.15 h at room temperature (RT=1.5 h), a control of the reaction advancement by TLC indicates the completion. The reaction was quenched by addition of 10% NaHCO$_3$ (2 mL) and stirred 15 min. Reaction mixture was diluted with DCM (50 mL) and washed with 10% citric acid (1×10 mL), H$_2$O (1×10 mL) and brine (1×10 mL). The organic phase was dried over Na$_2$SO$_4$, filtered and evaporated under reduced pressure. Crude mixture was separated by CC to give the hexapeptide Boc-Abu-D-MeAla-EtVal-Leu-MeLeu-Ala-OMe as a yellowish oil. A sample (30 mg) was repurified by semi-preparative RP-HPLC and the product lyophilized to give the hexapeptide Boc-Abu-D-MeAla-EtVal-Leu-MeLeu-Ala-OMe as a white powder.

2.9. Preparation of H-Abu-D-MeAla-EtVal-Leu-MeLeu-Ala-OMe Fragment (Bb)

A solution of the hexapeptide as obtained in the preceding reaction (0.187 g, 0.25 mmol, 1.0 equiv.) in TFA/DCM (3.0 mL, 2:3 v/v) was kept at 0° C. for 1.5 h, and the solvents removed under reduced pressure. The crude product was dried under high vacuum (0.5 h). Subsequently, DCM (3 mL) was added and the mixture was triturated at 0° C. with DIPEA to pH 7-8 (Lackmus-paper) to remove TFA. After evaporation and drying the crude amine H-Abu-D-MeAla-EtVal-Leu-MeLeu-Ala-OMe was used to the next coupling step without further purification. A sample of crude product (23 mg) was re-purified by semi-preparative RP-HPLC and the peptide was lyophilized to give Fragment (Ba) H-Abu-D-MeAla-EtVal-Leu-MeLeu-Ala-OMe as a white powder.

UPLC-ESI-MS (m/z) 641.259 [M+H]$^+$ ([C$_{32}$H$_{61}$N$_6$O$_7$]$^+$; calc. 641.4602).

3. Coupling of fragment (Aa) and fragment (Bb)

3.1. Preparation of H-D-Hiv-MeLeu-Leu-MeVal-MeBmt-Abu-D-MeAla-EtVal-Leu-MeLeu-Ala-OMe To a solution of the hexapeptide H-Abu-D-MeAla-EtVal-Leu-MeLeu-Ala-OMe as obtained in the preceding reaction (0.16 g, 0.25 mmol, 1.0 equiv.) in dry DCM (10 mL), cooled at 0° C., was added under argon DIPEA (0.214 mL, 1.26 mmol, 5.0 equiv.). Subsequently, after 5 min, HATU (0.12 g, 0.31 mmol, 1.25 equiv.) and the pentadepsipeptide H-D-Hiv-MeLeu-Leu-MeVal-MeBmt-OH (4) as obtained above (0.16 g, 0.25 mmol, 1.0 equiv.) were added in one portion. After 15 min at 0° C. then 1.15 h at room temperature (RT=1.5 h), a control of the reaction advancement by TLC indicates the completion. The reaction was quenched by addition of 10% NaHCO$_3$ (3 mL) and stirred 15 min. Reaction mixture was diluted with DCM (40 mL) and washed with 10% citric acid (1×8 mL), H$_2$O (1×8 mL) and brine (1×8 mL). The organic phase was dried over Na$_2$SO$_4$, filtered and evaporated under reduced pressure. Crude mixture was separated by CC to give the undecapeptide H-D-Hiv-MeLeu-Leu-MeVal-MeBmt- Abu-D-MeAla-EtVal-Leu-MeLeu-Ala-OMe as a white foam. An analytical sample (18 mg) was repurified by semi-preparative RP-HPLC and the product was lyophilized to give the undecapeptide H-D-Hiv-MeLeu-Leu-MeVal-MeBmt-Abu-D-MeAla-EtVal-Leu-MeLeu-Ala-OMe as a white powder.

3.2. Preparation of H-D-Hiv-MeLeu-Leu-MeVal-MeBmt-Abu-D-MeAla-EtVal-Leu-MeLeu-Ala-OH A solution of the undecapeptide methylester as obtained in the preceding reaction (0.27 g, 0.21 mmol, 1.0 equiv.) in THF (2.5 mL) was cooled to 0° C. in an ice-water bath, then 0.2 M LiOH (2.11 mL, 0.42 mmol, 2.0 equiv.) was added dropwise over 10 min. The cooling bath was then removed and the mixture (pH=12-13; Lackmus-paper) was stirred at room temperature for 1 h 20 min (TLC control). Subsequently, the solution was cooled to 0° C. and acidified with 1.0 M HCl to pH 3-4. The solution was evaporated under reduced pressure. The residue was dissolved in AcOEt (40 mL) and washed with 10% citric acid (1×8 mL), $H_2O$ (1×8 mL) and brine (1×8 mL). The organic phase was dried over $Na_2SO_4$, filtered and evaporated under reduced pressure. The crude mixture was separated by CC to give the acid H-D-Hiv-MeLeu-Leu-MeVal-MeBmt-Abu-D-MeAla-EtVal-Leu-MeLeu-Ala-OH as a white powder. The sample (40 mg) was repurified by semi-preparative RP-HPLC and the product was lyophilized to give the undecapeptide H-D-Hiv-MeLeu-Leu-MeVal-MeBmt-Abu-D-MeAla-EtVal-Leu-MeLeu-Ala-OH as a white powder.

4. Macrolactonisation: Preparation of cyclo-(MeBmt-Abu-D-MeAla-EtVal-Leu-MeLeu-Ala-D-Hiv-MeLeu-Leu-MeVal) (Ib)

To a solution of DMAP (0.048 g, 0.39 mmol, 4.0 equiv.) and benzotriazol-1-yloxytripyrrolidinophosphonium hexafluorophosphate (PyBOP) (0.102 g, 0.196 mmol, 2.0 equiv.) in DCM (12 mL) was added dropwise over 1.5 h a solution of the undecapeptide as obtained in the preceding reaction (0.124 g, 0.098 mmol, 1.0 equiv.) in DCM (4 mL). The mixture was stirred after the addition of acid was complete (RT=24 h), then transferred to a separating funnel. The solution was washed with 1 M HCl (2 mL) and the organic layer was separated and dried over $MgSO_4$, filtered, and concentrated under reduced pressure. The crude product was purified by column chromatography, thereby giving the cycloundecadepsipeptide cyclo-(MeBmt-Abu-D-MeAla-EtVal-Leu-MeLeu-Ala-D-Hiv-MeLeu-Leu-MeVal) (Ia) as a white solid. A sample (77 mg) was purified by semi-preparative RP-HPLC and the product was lyophilized to give the cycloundecadepsipeptide cyclo-(MeBmt-Abu-D-MeAla-EtVal-Leu-MeLeu-Ala-D-Hiv-MeLeu-Leu-MeVal) (Ib) as a white powder.

UPLC-ESI-MS (m/z) 1245.787 $[M+H]^+$ ($[C_{65}H_{117}N_{10}O_{13}]^+$; calc. 1245.8802), 623.465 $[M/2+H]^+$ (calc. 623.444).

Example 3

Preparation of cyclo-(MeBmt-Val-D-MeAla-EtVal-Leu-MeLeu-Ala-D-Hiv-MeLeu-Leu-MeVal) (Ih)

The preparation of (Ih) was conducted by analogy to the preparation of compound as described in Example 2.

Fragment (Bh) was prepared by applying similar reaction conditions as described in Example 2 for the preparation of Fragment (Bb). Then, fragment (Bh) was coupled to Fragment (Aa) by applying similar reaction conditions as described in Example 2.

The macrolactonisation was then conducted by applying similar conditions as described in Example 2a to result in the cycloundecadepsipeptide cyclo-(MeBmt-Val-D-MeAla-EtVal-Leu-MeLeu-Ala-D-Hiv-MeLeu-Leu-MeVal) (Ih) UPLC-ESI-MS (m/z) 1259.888 $[M+H]^+$ ($[C_{66}H_{119}N_{10}O_{13}]^+$; calc. 1259.8958); 1260.788 $[M+2H]^{2+}$ ($[C_{66}H_{120}N_{10}O_{13}]^{2+}$; calc. 1260.9037).

Example 4

Preparation of cyclo-(MeBmt-Abu-D-MeAla-MeVal-Leu-MeLeu-Ala-D-Hiv-MeLeu-Leu-MeVal) (Id)

Fragment H-Abu-D-MeAla-MeVal-Leu-MeLeu-Ala-OMe (Bd) was prepared by applying similar reaction conditions as described in Example 1 for the preparation of Fragment (Ba). Then, the coupling to Fragment (Aa) and the macrolactonisation were conducted by applying similar reaction conditions as described in Example 1 to result in the cycloundecadepsipeptide cyclo-(MeBmt-Abu-D-MeAla-MeVal-Leu-MeLeu-Ala-D-Hiv-MeLeu-Leu-MeVal) (Id).

UPLC-ESI-MS (m/z) 1261.888 $[M+H]^+$ ($[C_{66}H_{117}N_{10}O_{14}]^+$; calc. 1261.8751)

Example 5

Inhibitory Effects in a HCV Replicon System

To determine whether the cycloundecadepsipeptide compounds of the present invention have anti-HCV activity, experiments were carried out that compared inhibitory effects of these compounds in a HCV replicon system.

Assays used Huh 9-13 containing the hepatitis C virus genotype 1b Con1 replicon (Lohmann et al. 2001. J. Virol. 75:1437-1449; and Lohmann et al. 1999. Science. 285:110-113). Cells were sub-cultured in cell growth medium DMEM supplemented with 10% FCS, 1% non-essential amino acids, 1% penicillin/streptomycin and 2% Geneticin (Invitrogen) at a ratio of 1:4-1:5 and grown for 3-4 days in 75 $cm^2$ tissue culture flasks (Techno Plastic Products), were harvested and seeded in assay medium (DMEM, 10% FCS, 1% non-essential amino acids, 1% penicillin/streptomycin) at a density of 5 000 cells/well (100 μl/well) in 96-well tissue culture microtiter plates (Falcon, Beckton Dickinson) for evaluation of cytostatic/cytotoxic and antiviral effect. The microtiter plates were incubated overnight (37° C., 5% $CO_2$, 95-99% relative humidity), yielding a non-confluent cell monolayer.

Cell density and cytostatic effects were estimated in parallel cultures in regular 96-well plates (Beckton-Dickinson) using the MTT assay (CellTiter 96 AQueous Non-Radioactive Cell Proliferation Assay, Promega). In this assay, 3-(4,5-dimethyl-thiazol-2-yl)-5-(3-carboxymethoxy-phenyl)-2-(4-sulfophenyl)-2H-tetrazolium (MTS) is bioreduced to a formazan that is quantified at 498 nm in a plate reader. Formazan production is directly correlated with number of life cells. Absorbance was measured at a wavelength of 498 nm (Safire$^2$, Tecan) and optical densities (OD values) were converted to percentage of untreated controls.

The compounds were dissolved in DMSO at a concentration of 4 mmole/L. Stock solutions were immediately used to set up the experiments. The compounds were tested at 24 different concentrations ranging from 0.0001 μmole/L to 100 μmole/L. The highest concentration of DMSO in the assay was determined to be 2.5% (at 100 μM final concentration of the compound). During the assay setup, the DMSO percentage decreased concomitantly with decrease in concentration of the compound.

For the evaluation of antiviral effects, assay medium was aspirated and the plates with dry monolayer were stored at −80° C. awaiting extraction. Following thawing of the plates at room temperature, the cell monolayer was lysed with 100 μl of cell-to-cDNA lysis buffer (Invitrogen). Lysis of the cells was allowed to proceed for 10 min at room temperature after which all liquid was transferred to a PCR plate (Axygen). The PCR plate was incubated for 15 min at 75° C. (T3, Biometra). The lysate was diluted 1:2 with RNase/DNase-free water, after which 5 μl was transferred to the real-time PCR plate (Applied Biosystems).

Replicon RNA content was quantified using a real-time quantitative one-step RT-PCR method (RT-qPCR): Low Rox One-Step RT-qPCR master mix, Abgene). The forward and reverse primers used were 5'-CCA GAT CAT CCT GAT CGA CCA G-3' and 5'-CCG GCT ACC TGC CCA TTC-3', respectively. The fluorogenic probe was 5'-ACATCGCATCGAGC-GAGCACGTAC-3'. The analysis of the samples were performed using a SDS7500F (Applied Biosystems, standard thermocycling profile: 30 min at 48° C., 10 min at 95° C., 40 cycles of 15 sec at 95° C. and 1 min at 60° C.) after which replicon RNA quantities were converted to percentage of untreated controls.

The $EC_{50}$ (value derived from the dose-response curve) represents the concentration at which 50% inhibition of viral replication is observed. The $CC_{50}$ (value derived from the dose-response curve) represents the concentration at which the metabolic activity of the cells is reduced to 50% of the metabolic activity of untreated cells.

Results from these experiments permitted calculation of $EC_{50} \pm SD$ (standard deviation or Std. Dev.), which is the effective concentration required to inhibit HCV replicon replication by 50%, and of $CC_{50} \pm SD$ (whenever possible), which is the concentration required that inhibits the proliferation of exponentially growing cells by 50%. $EC_{50}$ and $CC_{50} \pm SD$ values were calculated respectively as the median of all the $EC_{50}$, or $CC_{50}$ values derived from the 3 individual dose-response curves. The selectivity index (SI), indicative of the therapeutic window of the compound was calculated as the ratio between $CC_{50}$ and $EC_{50}$.

Table 1 shows the results of the comparison of the $EC_{50}$, $CC_{50}$ (μmole/L) and SI values of the selected compounds in the Huh 9-13 cells.

TABLE 1

| Compound | $EC_{50}$ (μmole/L) | | $CC_{50}$ (μmole/L) | | SI |
|---|---|---|---|---|---|
| | mean | sd | mean | sd | |
| Debio 025 | 0.034 | 0.02 | 2.5 | 0.6 | 73.5 |
| (Ia) | 0.034 | 0.019 | 60.1 | | 1791.8 |
| (Ib) | 0.037 | 0.023 | 52.3 | | 1398 |
| (Ic) | 0.022 | 0.006 | 86.9 | | 4024.1 |
| (Id) | 0.025 | 0.013 | 44.4 | | 1745.9 |
| (Ie) | 0.07 | 0.02 | 8.3 | 3.3 | 117.9 |
| (If) | 0.025 | 0.02 | 81.8 | | 3236.8 |
| (Ig) | 0.033 | 0.016 | 67 | | 2045.2 |
| (Ih) | 0.022 | 0.02 | 20.5 | | 950 |
| (Ii) | 0.041 | 0.023 | 25.4 | | 623.8 |
| (Ik) | 0.075 | 0.033 | 9.8 | 0.9 | 132 |

A concentration of compound is considered to elicit a genuine antiviral effect in the HCV replicon system when, at that particular concentration, the anti-replicon effect is well above the 70% threshold and no more than 30% reduction in metabolic activity is observed.

As shown in table 1, these results obtained in Huh 9-13 cells show that these compounds selectively inhibit the replication of hepatitis C virus replicon in cell culture and demonstrate similar to higher potency than Debio 025 with $EC_{50}$ values in the double digit nanomolar range and similar to higher selectivity indexes.

Example 6

Non-Immunosuppression Activity

To determine whether the cycloundecadepsipepide compounds of the present invention have a non-immunosuppression activity, experiments were carried out that compared the dose-dependent inhibition of Concanavalin-A-induced T-cell proliferation (see Table 2).

The method of the assays were performed as described by Dayton et al. (1992. Mol. Pharmacol. 41. 671-676) and Mishell et al. (1980. Cell proliferation in selected methods in cellular immunology, V, XXIX, W.H. Freeman Co., San Francisco, Calif. 153-160). The $IC_{50}$ (half maximal inhibitory concentration) of the compounds was derived from the dose response curve and compared to the $IC_{50}$ of CsA ($IC_{50}$ ratio).

TABLE 2

| Compound | $IC_{50}$ (micromole/L) | $IC_{50}$ ratio |
|---|---|---|
| Cyclosporin A (CsA) | 0.006 | 1 |
| (Ia) | 2 | 333 |
| (Ib) | 9.44 | 1573 |
| (Ic) | 0.984 | 164 |
| (Id) | 1.435 | 239 |
| (Ie) | 2 | 333 |
| (If) | 7.725 | 1288 |
| (Ig) | 2.69 | 448 |
| (Ih) | 1.74 | 290 |
| (Ii) | 2.69 | 448 |
| (Ik) | 3.44 | 573 |

In this study, Compounds (Ia), (Ib) and (Id) are at least ca. 300 fold less immunosuppressive than cyclosporine A (CsA) (in term of IC50 ratio).

Example 7

Hepatic Transporters Interactions

To determine whether the cycloundecadepsipeptide compounds of the present invention interact with hepatic transporters, experiments were carried out that compared the concentration-dependent inhibition towards the multidrug resistance associated protein 2 (MRP2), the organic anion transporting polypeptide 1B1 (OATP1B1), the bile salt export pump (BSEP) and the sodium-taurocholate cotransporting polypeptide (NTCP). These transporters are involved in the hepatobiliary circulation of endogenous compounds such as bile salts or bilirubin (for a review, see C. Pauli-Magnus et al, J. Hepatology, 2005, 43:342-357). Some of them also contribute to the elimination of xenobiotics.

MRP2 and BSEP were expressed by SOLVO Biotechnology in *Spodoptera frugiperda* (Sf9) ovarian cells, by infecting the insect cells with a recombinant baculovirus. The inhibition of the transport of the radioactive probe substrates (estradiol-17-beta-glucuronide and taurocholate for MRP2 and BSEP, respectively) into inside-out membrane vesicles, containing the transporter, was measured by scintillation counting.

OATP1B1 and NTCP assays were performed with Chinese hamster ovary (CHO) cells expressing these human uptake transporters. The amount of the transported probe substrate (estrone-3-sulfate and taurocholate for OATP1B1 and NTCP, respectively) was determined by liquid scintillation or fluorescent photometry after cell lysis.

The $IC_{50}$ (defined as the concentration required for inhibiting the transport of the probe substrate by 50%, half maximal inhibitory concentration) of the compounds was derived from the concentration-response curve and compared to the $IC_{50}$ of Debio 025 ($IC_{50}$ ratio expressed as "fold Debio 025" in the tables).

MRP2 is the main driving force for bile-salts independent bile flow and transports a wide spectrum of organic anions including bilirubin-diglucuronide, bile salts conjugates as well as several drugs. Table 3 shows the results of the interaction of the selected compounds towards this transporter.

TABLE 3

| MRP2 | | |
|---|---|---|
| | $IC_{50}$ (µM) | fold Debio 025 |
| Debio 025 | 15 | 1 |
| (Ib) | n.i. | n.a. |
| (Ih) | n.i. | n.a. |
| (Id) | n.i. | n.a. |
| (Ie) | 20 | 0.73 |
| (Ic) | 2.2 | 6.6 |
| (Ia) | n.i. | n.a. |
| (If) | n.i. | n.a. | n.i. no inhibition
n.a. not applicable

OATP1B1 transports bile salts in a sodium-independent manner. Furthermore, numerous drugs are substrates of OATPs. Table 4 shows the results of the interaction of the selected compounds towards OATP1B1.

TABLE 4

| OATP1B | | |
|---|---|---|
| | $IC_{50}$ (µM) | fold Debio 025 |
| Debio 025 | 0.42 | 1 |
| (Ib) | 6.2 | 0.07 |
| (Ih) | 12 | 0.04 |
| (Id) | 7.9 | 0.05 |
| (Ie) | 0.58 | 0.72 |
| (Ic) | 2.3 | 0.18 |
| (Ia) | 18 | 0.02 |
| (If) | 15 | 0.03 |

BSEP is the main bile salts efflux system involved in the secretion of the cholephilic compounds from the liver cell into the bile canaliculus. Table 5 shows the results of the interaction of the selected compounds towards BSEP.

TABLE 5

| BSEP | | |
|---|---|---|
| | $IC_{50}$ (µM) | fold Debio 025 |
| Debio 025 | 0.24 | 1 |
| (Ib) | 0.15 | 1.6 |
| (Ih) | 0.30 | 0.80 |
| (Id) | 0.57 | 0.42 |
| (Ie) | 0.60 | 0.40 |
| (Ic) | 0.16 | 1.5 |
| (Ia) | 0.40 | 0.60 |
| (If) | 0.48 | 0.50 |

NTCP mediates the sodium-dependent uptake of bile salts from portal circulation, which is essential for bile formation. Table 6 shows the results of the interaction of the selected compounds towards NTCP.

TABLE 6

| NTCP | | |
|---|---|---|
| | $IC_{50}$ (µM) | fold Debio 025 |
| Debio 025 | 3.2 | 1 |
| (Ib) | 65 | 0.05 |
| (Ih) | n.i. | na |
| (Id) | 2.5 | 1.2 |
| (Ie) | 26 | 0.12 |
| (Ic) | 30 | 0.11 |
| (Ia) | n.i. | na |
| (If) | n.i. | na | n.i. no inhibition
n.a. not applicable

Apart from these in vitro investigations on hepatic transporters, the cycloundecadepsipeptide compounds of the present invention were also evaluated with respect to in vitro inhibition of metabolic enzymes, as well as pharmacokinetic properties in animals in vivo.

As shown in tables 3-6, the results from the in vitro transport experiments show that these compounds demonstrate a much lower potency to inhibit some hepatic transporters as compared to Debio 025. In particular, some compounds show an absence of inhibition towards MRP2 and/or up to 50-fold lower potency towards OATP1B1. Therefore, these compounds are expected to either reduce the potential adverse effects (e.g. hyperbilirubinemia) related to the inhibition of hepatic transporters, or the potential drug-drug interactions (e.g. with HMG-CoA reductase inhibitors such as atorvastatin) related to the inhibition of hepatic transporters, or even both.

LIST OF ABBREVIATIONS

| | |
|---|---|
| Abu | L-α-amino-n-butyric acid |
| Ac | acetyl |
| AcOEt | ethyl acetate |
| AcOH | acetic acid |
| Ala | L-alanine |
| Boc | tert-butyloxycarbonyl |
| BSEP | bile salt export pump |
| t-Bu | tert-butyl |
| Ca(MeO)$_2$ | calcium methoxide |
| CC | column chromatography |
| DCM | dichloromethane |
| DIPEA | N,N-diisopropylethylamine |
| DMAP | 4-(N,N-dimethylamino)pyridine |
| DMSO | dimethyl sulfoxide |
| Eq | equivalent |
| ESI-MS | electrospray ionization mass spectrometry |
| EtVal | N-ethyl-L-valine |
| Fmoc | 9-fluorenylmethoxycarbonyl |
| HATU | N-[(dimethylamino)-1H-1,2,3-triazolo[4,5-b]pyridine-1-yl-methylene]-N-methylmethanaminium hexafluorophosphate N-oxide |
| D-Hiv | D-hydroxyisovaleric acid |
| g | gramme |
| HCOOH | formic acid |
| HPLC | high performance liquid chromatography |
| HR-MALDI-MS | high resolution MALDI-TOF mass spectrometry |
| HR-Q-TOF-MS | high resolution Q-TOF mass spectrometry |
| Im$_2$CO | N,N-carbonyl-dimidazole (CDI) |
| Kg | kilogramme |

-continued

| | |
|---|---|
| KOMe | potassium methoxide |
| L | liter |
| MALDI | matrix-assisted laser desorption/ionization |
| MALDI-TOF | time-of-flight mass spectrometry |
| Me | methyl |
| D-MeAla | N-methyl-D-alanine |
| MeBmt | N-methyl-(4R)-4-[(E)-2-butenyl]-4,4-dimethyl-L-threonine |
| MeLeu | N-methyl-L-leucine |
| MeCN | acetonitrile |
| MeOH | methanol |
| MeVal | N-methyl-L-valine |
| mg | milligramme |
| mL | milliliter |
| MRP2 | multidrug resistance associated protein 2 |
| MS | mass spectrometry |
| MtBE | methyl-tertio-butyl-ether |
| NMR | nuclear magnetic resonance |
| NTCP | sodium-taurocholate cotransporting polypeptide |
| OATP1B1 | organic anion transporting polypeptide 1B1 |
| PyBOP | (benzotriazol-1-yloxy)-tris(pyrrolidino)phosphonium-hexafluorophosphate |
| RP | reverse-phase |
| RP-HPLC | reverse-phase HPLC |
| RT | reaction time |
| Thr | L-threonine |
| TFA | trifluoroacetic acid |
| $t_R$ | retention time |
| THF | tetrahydrofuran |
| Tj | temperature of the jacket |
| TLC | thin layer chromatography |
| Tr | temperature into the reactor |
| UPLC | ultra performance liquid chromatography |
| Vol. | volumes (1 g of key raw material means 1 volume) |

The invention claimed is:

1. A cycloundecadepsipeptide compound of Formula (I)

$$\text{Cyclo-(AXX}_1\text{-AXX}_2\text{-AXX}_3\text{-AXX}_4\text{-AXX}_5\text{-AXX}_6\text{-AXX}_7\text{-D-Hiv-MeLeu-Leu-Meval)} \quad (I)$$

in which:
AXX$_1$ is MeBmt, 4-fluoro-MeBmt, dihydro-MeBmt, 8-hydroxy-MeBmt, or O-acetyl-MeBmt;
AXX$_2$ is Abu, Val, Thr, Thr(OMe), Thr(OAc), Thr(OCOCH$_2$CH$_2$CH$_2$OH), Nva, or 5-hydroxy-Nva;
AXX$_3$ is D-MeAla, D-3-fluoro-MeAla, D-MeSer, D-MeSer(OAc), D-MeSer(OCH$_2$CH$_{20}$H), D-MeSer(OCH$_2$CH$_2$NEt$_2$), or D-MeAsp(OMe);
AXX$_4$ is MeIle, MeMet, MeVal, MeThr, MeThr(OAc), MeAla, EtVal, EtIle, EtPhe, EtTyr, EtThr(OAc), MeThr(OAc), MeTyr, MeTyr(OAc), MeTyr(OMe), MePhe, or MeMet(Ox), wherein the sulphur atom of methionine is sulphoxyde or sulphone;
AXX$_5$ is Leu, Val, or Ile;
AXX$_6$ is MeAla, Sar, or MeLeu; and
AXX$_7$ is Gly or Ala.

2. The compound according to claim 1, wherein, in Formula (I),
AXX$_1$ is MeBmt or 8-hydroxy-MeBmt;
AXX$_2$ is Abu, Val, Thr, Thr(OMe), Thr(OAc), Thr(OCOCH$_2$CH$_2$CH$_{20}$H), or 5-hydroxy-Nva;
AXX$_3$ is D-MeAla, D-3-fluoro-MeAla, D-MeSer, D-MeSer(OAc), or D-MeAsp(OMe);
AXX$_4$ is MeIle, MeMet, MeMet(Ox) wherein Ox is —SOMe or —SO$_2$Me, MeVal, EtVal, EtIle, or MeTyr; and
AXX$_5$ is Leu, Val, or Ile;
AXX$_6$ is MeAla, Sar, or MeLeu; and
AXX$_7$ is Gly or Ala.

3. The compound according to claim 1, wherein
AXX$_1$ is MeBmt;
AXX$_2$ is Abu, Val, or Thr;
AXX$_3$ is D-MeAla;
AXX$_4$ is MeIle, MeVal, or EtVal;
AXX$_5$ is Leu, Val, or Ile;
AXX$_6$ is MeAla, MeLeu, or Sar; and
AXX$_7$ is Gly or Ala.

4. The compound according to claim 1, having the following formulae:

| | |
|---|---|
| cyclo-(MeBmt-Abu-D-MeAla-MeVal-Leu-MeLeu-Gly-D-Hiv-MeLeu-Leu-MeVal) | (Ia); |
| cyclo-(MeBmt-Abu-D-MeAla-EtVal-Leu-MeLeu-Ala-D-Hiv-MeLeu-Leu-MeVal) | (Ib); |
| cyclo-(MeBmt-Val-D-MeAla-MeVal-Ile-MeLeu-Gly-D-Hiv-MeLeu-Leu-MeVal) | (Ic); |
| cyclo-(MeBmt-Abu-D-MeAla-MeVal-Leu-MeLeu-Ala-D-Hiv-MeLeu-Leu-MeVal) | (Id); |
| cyclo-(MeBmt-Abu-D-MeAla-MeVal-Val-MeAla-Ala-D-Hiv-MeLeu-Leu-MeVal) | (Ie); |
| cyclo-(MeBmt-Val-D-MeAla-MeVal-Leu-MeLeu-Gly-D-Hiv-MeLeu-Leu-MeVal) | (If); |
| cyclo-(MeBmt-Abu-D-MeAla-MeVal-Ile-MeLeu-Gly-D-Hiv-MeLeu-Leu-MeVal) | (Ig); |
| cyclo-(MeBmt-Val-D-MeAla-EtVal-Leu-MeLeu-Ala-D-Hiv-MeLeu-Leu-MeVal) | (Ih); |
| cyclo-(MeBmt-Abu-D-MeAla-MeIle-Leu-MeLeu-Gly-D-Hiv-MeLeu-Leu-MeVal) | (Ii); or |
| cyclo-(MeBmt-Val-D-MeAla-MeVal-Val-Sar-Gly-D-Hiv-MeLeu-Leu-MeVal) | (Ik). |

5. A pharmaceutical composition comprising the compound according to claim 1, and one or more pharmaceutically acceptable diluents or carriers.

6. A pharmaceutical combination comprising at least a) a first agent consisting of the compound according to claim 1, and b) a second agent having properties to act against HCV replication.

7. A method for treating a Hepatitis C infection or a HCV induced disorder in a subject in need thereof, comprising administering to said subject the pharmaceutical combination of claim 6.

8. A method for inhibiting viral replication, comprising administering the compound according to claim 1 to an infected cell or organism.

9. A method for treating a Hepatitis C infection or a HCV induced disorder in a subject in need thereof, comprising administering to said subject a therapeutically effective amount of the compound according to claim 1.

10. A method for inhibiting HCV replication in a patient in need thereof, comprising administering to said subject a therapeutically effective amount of the compound according to claim 1.

11. A method for treating a Hepatitis C infection or a HCV induced disorder in a subject in need thereof, comprising co-administering concomitantly or in sequence, a therapeutically effective amount of the compound according to claim 1 and at least a second agent having anti-HCV properties.

12. The method of claim 11, wherein said agent having anti-HCV properties is selected from the group consisting of an interferon; an anti-viral agent; an inhibitor of HCV encoded factors; an anti-fibrotic agent; an immune modulating agent; and a S1 P receptor agonist.

13. A pharmaceutical combination comprising at least a) a first agent consisting of the pharmaceutical composition according to claim 5, and b) a second agent having properties to act against HCV replication.

14. A method for treating a Hepatitis C infection or a HCV induced disorder in a subject in need thereof, comprising administering to said subject a therapeutically effective amount of the pharmaceutical composition according to claim 5.

15. A method for inhibiting HCV replication in a patient in need thereof, comprising administering to said subject a therapeutically effective amount of the pharmaceutical composition according to claim 5.

16. A method for treating a Hepatitis C infection or a HCV induced disorder in a subject in need thereof, comprising co-administering, concomitantly or in sequence, a therapeutically effective amount of the pharmaceutical composition according to claim 5 and at least a second agent having anti-HCV properties.

17. The method according to claim 12, wherein said interferon is interferon-alpha-2a, interferon-alpha-2b, an interferon conjugated to a water soluble polymer, or an interferon conjugated to human albumin; said anti-viral agent is ribavirin, lamivudine, NV08, or NM283; said inhibitor of HCV encoded factors inhibits NS3-4A protease, helicase, or RNA polymerase; said anti-fibrotic agent is an N-phenyl-2-pyrimidine-amine derivative; said immune modulating agent is mycophenolic acid; and said S1 P receptor agonist is FTY720 or an analogue thereof.

18. The method according to claim 17, wherein said S1 P receptor agonist is phosphorylated.

* * * * *